(12) United States Patent
Venet et al.

(10) Patent No.: US 6,420,387 B1
(45) Date of Patent: *Jul. 16, 2002

(54) FARNESYL PROTEIN TRANSFERASE INHIBITING (IMIDAZOL-5-YL) METHYL-2-QUINOLINONE DERIVATIVES

(75) Inventors: Marc Gaston Venet, Le Mesnil Esnard; Patrick René Angibaud, Fontaine-Bellenger; Philippe Muller, Andé; Gérard Charles Sanz, Le Mesnil Esnard, all of (FR)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/689,211

(22) Filed: Oct. 12, 2000

Related U.S. Application Data

(63) Continuation of application No. 09/363,353, filed on Jul. 29, 1999, which is a continuation of application No. 08/084,717, filed as application No. PCT/EP96/04515 on Oct. 16, 1996, now Pat. No. 6,037,350.

(30) Foreign Application Priority Data

Dec. 8, 1995 (EP) .............................. 95203427

(51) Int. Cl.$^7$ ..................... A61K 31/445; C02D 215/16
(52) U.S. Cl. ....................................... 514/312; 546/157
(58) Field of Search ........................ 546/157; 514/312

(56) References Cited

U.S. PATENT DOCUMENTS 6,037,350 A * 3/2000 Venet ........................ 514/312

FOREIGN PATENT DOCUMENTS

| EP | 0 371 564 A | 6/1990 |
|---|---|---|
| GB | 2 101 115 | 1/1983 |

* cited by examiner

Primary Examiner—D. Margaret Seaman

(57) ABSTRACT

This invention comprises the novel compounds of formula (I)

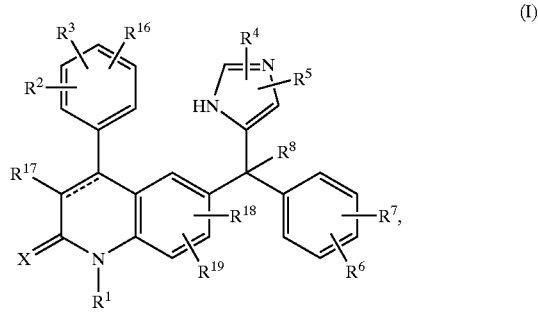

wherein the dotted line represents an optional bond; X is oxygen or sulfur; $R^1$ is hydrogen, $C_{1-12}$alkyl, $Ar^1$, $Ar^2C_{1-6}$alkyl, quinolinyl$C_{1-6}$alkyl, pyridyl$C_{1-6}$alkyl, hydroxy$C_{1-6}$alkyl, $C_{1-6}$alkyloxy$C_{1-6}$alkyl, mono- or di($C_{1-6}$alkyl)amino$C_{1-6}$alkyl, amino$C_{1-6}$alkyl, or a radical of formula $-Alk^1-C(=O)-R^9$, $-Alk^1-S(O)-R^9$ or $-Alk^1-S(O)_2-R^9$; $R^2$, $R^3$ and $R^{16}$ each independently are hydrogen, hydroxy, halo, cyano, $C_{1-6}$alkyl, $C_{1-6}$alkyloxy, hydroxy$C_{1-6}$akyloxy, $C_{1-6}$alkyloxy$C_{1-6}$alkyloxy, amino$C_{1-6}$alkyloxy, mono- or di($C_{1-6}$alkyl)amino $C_{1-6}$alkyloxy, $Ar^1$, $Ar^2C_{1-6}$alkyl, $Ar^2$oxy, $Ar^2C_{1-6}$alkyloxy, hydroxycarbonyl, $C_{1-6}$alkyloxycarbonyl, trihalomethyl, trihalomethoxy, $C_{2-6}$alkenyl; $R^4$ and $R^5$ each independently are hydrogen, halo, $Ar^1$, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O) $C_{1-6}$alkyl or $C_{1-6}$alkylS(O)$_2C_{1-6}$alkyl; $R^6$ and $R^7$ each independently are hydrogen, halo, cyano, $C_{1-6}$alkyl, 4,4-dimethyl-oxazolyl, $C_{1-6}$alkyloxy or $Ar^2$oxy; $R^8$ is hydrogen, $C_{1-6}$alkyl, cyano, hydroxycarbonyl, $C_{1-6}$alkyloxycarbonyl, $C_{1-6}$alkylcarbonyl$C_{1-6}$alkyl; cyano$C_{1-6}$alkyl, $C_{1-6}$alkyloxycarbonyl$C_{1-6}$alkyl, carboxy$C_{1-6}$alkyl, hydroxy$C_{1-6}$alkyl, amino$C_{1-6}$alkyl, mono- or di($C_{1-6}$alkyl) amino$C_{1-6}$alkyl, imidazolyl, halo$C_{1-6}$alkyl, $C_{1-6}$alkyloxy $C_{1-6}$alkyl, aminocarbonyl$C_{1-6}$alkyl, or a radical of formula $-O-R^{10}$, $-SR^{10}$, $-N-R^{11}R^{12}$; $R^{17}$ is hydrogen, halo, cyano, $C_{1-6}$alkyl, $C_{1-6}$alkyloxycarbonyl, $Ar^1$; $R^{18}$ is hydrogen, $C_{1-6}$alkyl, $C_{1-6}$alkyloxy or halo; $R^{19}$ is hydrogen or $C_{1-6}$alkyl; having farnesyl transferase inhibiting activity; their preparation, compositions containing them and their use as a medicine.

2 Claims, No Drawings

FARNESYL PROTEIN TRANSFERASE INHIBITING (IMIDAZOL-5-YL) METHYL-2-QUINOLINONE DERIVATIVES

CROSS REFERENCE TO RELATED APPLICATIONS

This application is a continuation of U.S. application Ser. No. 09/363,353, filed Jul. 29, 1999 which is continuation of U.S. application Ser. No. 09/084,717, filed May 26, 1997 now U.S. Pat. No. 6,037,350, which was the National Stage application under 35 U.S.C. §371 of International Application No. PCT/EP96/04515 filed Oct. 16, 1996, which claims priority from EP95.203.427.0, filed Dec. 8, 1995, the contents of all of which are hereby incorporated by reference.

The present invention is concerned with novel (imidazol-5-yl)methyl-2-quinolinone derivatives, the preparation thereof, pharmaceutical compositions comprising said novel compounds and the use of these compounds as a medicine as well as methods of treatment by administering said compounds.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer. A particular group of oncogenes is known as ras which have been identified in mammals, birds, insects, mollusks, plants, fungi and yeasts. The family of mammalian ras oncogenes consists of three major members ("isoforms"): H-ras, K-ras and N-ras oncogenes. These ras oncogenes code for highly related proteins generically known as $p21^{ras}$. Once attached to plasma membranes, the mutant or oncogenic forms of $p21^{ras}$ will provide a signal for the transformation and uncontrolled growth of malignant tumor cells. To acquire this transforming potential, the precursor of the $p21^{ras}$ oncoprotein must undergo an enzymatically catalyzed farnesylation of the cysteine residue located in a carboxyl-terminal tetrapeptide. Therefore, inhibitors of the enzyme that catalyzes this modification, farnesyl protein transferase, will prevent the membrane attachment of $p21^{ras}$ and block the aberrant growth of ras-transformed tumors. Hence, it is generally accepted in the art that farnesyl transferase inhibitors can be very useful as anticancer agents for tumors in which ras contributes to transformation.

Since mutated, oncogenic forms of ras are frequently found in many human cancers, most notably in more than 50% of colon and pancreatic carcinomas (Kohl et al., Science, vol 260, 1834–1837, 1993), it has been suggested that farnesyl tranferase inhibitors can be very useful against these types of cancer.

In EP-0,371,564 there are described (1H-azol-1-ylmethyl) substituted quinoline and quinolinone derivatives which suppress the plasma elimination of retinoic acids. Some of these compounds also have the ability to inhibit the formation of androgens from progestines and/or inhibit the action of the aromatase enzyme complex.

Unexpectedly, it has been found that the present novel compounds, all having a phenyl substituent on the 4-position of the 2-quinolinone-moiety and wherein the imidazole moiety is bound via a carbon atom to the rest of the molecule, show farnesyl protein transferase inhibiting activity.

The present invention encompasses compounds of formula (I)

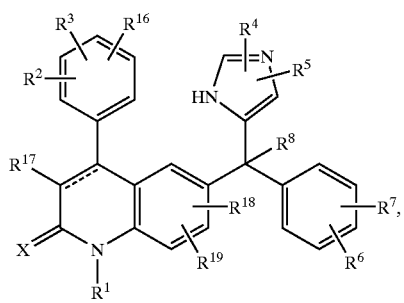

the pharmaceutically acceptable acid or base addition salts and the stereochemically isomeric forms thereof, wherein the dotted line represents an optional bond;

X is oxygen or sulfur;

$R^1$ is hydrogen, $C_{1-12}$alkyl, $Ar^1$, $Ar^2C_{1-6}$alkyl, quinolinyl$C_{1-6}$alkyl, pyridyl$C_{1-6}$alkyl, hydroxy$C_{1-6}$alkyl, $C_{1-6}$alkyloxy$C_{1-6}$alkyl, mono- or di($C_{1-6}$alkyl)amino$C_{1-6}$alkyl, amino$C_{1-6}$alkyl, or a radical of formula —Alk$^1$—C(=O)—R$^9$, —Alk$^1$—S(O)—R$^9$ or —Alk$^1$—S(O)$_2$—R$^9$, wherein Alk$^1$ is $C_{1-6}$alkanediyl, $R^9$ is hydroxy, $C_{1-6}$alkyl, $C_{1-6}$alkyloxy, amino, $C_{1-8}$alkylamino or $C_{1-8}$alkylamino substituted with $C_{1-6}$alkyloxycarbonyl;

$R^2$, $R^3$ and $R^{16}$ each independently are hydrogen, hydroxy, halo, cyano, $C_{1-6}$alkyl, $C_{1-6}$alkyloxy, hydroxy$C_{1-6}$alkyloxy, $C_{1-6}$alkyloxy$C_{1-6}$alkyloxy, amino$C_{1-6}$alkyloxy, mono- or di($C_{1-6}$alkyl)amino $C_{1-6}$alkyloxy, $Ar^1$, $Ar^2C_{1-6}$alkyl, $Ar^2$oxy, $Ar^2C_{1-6}$alkyloxy, hydroxycarbonyl, $C_{1-6}$alkyloxycarbonyl, trihalomethyl, trihalomethoxy, $C_{2-6}$alkenyl, 4,4-dimethyloxazolyl; or when on adjacent positions $R^2$ and $R^3$ taken together may form a bivalent radical of formula

| | |
|---|---|
| —O—CH$_2$—O— | (a-1), |
| —O—CH$_2$—CH$_2$—O— | (a-2), |
| —O—CH=CH— | (a-3), |
| —O—CH$_2$—CH$_2$— | (a-4), |
| —O—CH$_2$—CH$_2$—CH$_2$— | (a-5), or |
| —CH=CH—CH=CH— | (a-6); |

$R^4$ and $R^5$ each independently are hydrogen, halo, $Ar^1$, $C_{1-6}$alkyl, hydroxy$C_{1-6}$alkyl, $C_{1-6}$alkyloxy$C_{1-6}$alkyl, $C_{1-6}$alkyloxy, $C_{1-6}$alkylthio, amino, hydroxycarbonyl, $C_{1-6}$alkyloxycarbonyl, $C_{1-6}$alkylS(O)$C_{1-6}$alkyl or $C_{1-6}$alkylS(O)$_2$$C_{1-6}$alkyl;

$R^6$ and $R^7$ each independently are hydrogen, halo, cyano, $C_{1-6}$alkyl, $C_{1-6}$alkyloxy, $Ar^2$oxy, trihalomethyl, $C_{1-6}$alkylthio, di($C_{1-6}$alkyl)amino, or when on adjacent positions $R^6$ and $R^7$ taken together may form a bivalent radical of formula

| | |
|---|---|
| —O—CH$_2$—O— | (c-1), or |
| —CH=CH—CH=CH— | (c-2); |

$R^8$ is hydrogen, $C_{1-6}$alkyl, cyano, hydroxycarbonyl, $C_{1-6}$alkyloxycarbonyl, $C_{1-6}$alkylcarbonyl$C_{1-6}$alkyl, cyanoC$_{1-6}$alkyl, C$_{1-6}$alkyloxycarbonylC$_{1-6}$alkyl, carboxyC$_{1-6}$alkyl, hydroxyC$_{1-6}$alkyl, aminoC$_{1-6}$alkyl, mono- or di(C$_{1-6}$alkyl)aminoC$_{1-6}$alkyl, imidazolyl, haloC$_{1-6}$alkyl, C$_{1-6}$alkyloxyC$_{1-6}$alkyl, aminocarbonylC$_{1-6}$alkyl, or a radical of formula $$—O—R^{10} \quad (b-1),$$

$$—S—R^{10} \quad (b-2),$$

$$—N—R^{11}R^{12} \quad (b-3),$$

wherein R$^{10}$ is hydrogen, C$_{1-6}$alkyl, C$_{1-6}$alkylcarbonyl, Ar$^1$, Ar$^2$C$_{1-6}$alkyl, C$_{1-6}$alkyloxycarbonylC$_{1-6}$alkyl, or a radical or formula —Alk$^2$—OR$^{13}$ or —Alk$^2$—NR$^{14}$R$^{15}$;

R$^{11}$ is hydrogen, C$_{1-12}$alkyl, Ar$^1$ or Ar$^2$C$_{1-6}$alkyl;

R$^{12}$ is hydrogen, C$_{1-6}$alkyl, C$_{1-6}$alkylcarbonyl, C$_{1-6}$alkyloxycarbonyl, C$_{1-6}$alkylaminocarbonyl, Ar$^1$, Ar$^2$C$_{1-6}$alkyl, C$_{1-6}$alkylcarbonylC$_{1-6}$alkyl, a natural amino acid, Ar$^1$carbonyl, Ar$^2$C$_{1-6}$alkylcarbonyl, aminocarbonylcarbonyl, C$_{1-6}$alkyloxyC$_{1-6}$alkylcarbonyl, hydroxy, C$_{1-6}$alkyloxy, aminocarbonyl, di(C$_{1-6}$alkyl)aminoC$_{1-6}$alkylcarbonyl, amino, C$_{1-6}$alkylamino, C$_{1-6}$alkylcarbonylamino, or a radical or formula —Alk$^2$—OR$^{13}$ or —Alk$^2$—NR$^{14}$R$^{15}$;

wherein Alk$^2$ is C$_{1-6}$alkanediyl;

R$^{13}$ is hydrogen, C$_{1-6}$alkyl, C$_{1-6}$alkylcarbonyl, hydroxyC$_{1-6}$alkyl, Ar$^1$ or Ar$^2$C$_{1-6}$alkyl;

R$^{14}$ is hydrogen, C$_{1-6}$alkyl, Ar$^1$ or Ar$^2$C$_{1-6}$alkyl;

R$^{15}$ is hydrogen, C$_{1-6}$alkyl, C$_{1-6}$alkylcarbonyl, Ar$^1$ or Ar$^2$C$_{1-6}$alkyl;

R$^{17}$ is hydrogen, halo, cyano, C$_{1-6}$alkyl, C$_{1-6}$alkyloxycarbonyl, Ar$^1$;

R$^{18}$ is hydrogen, C$_{1-6}$alkyl, C$_{1-6}$alkyloxy or halo;

R$^{19}$ is hydrogen or C$_{1-6}$alkyl;

Ar$^1$ is phenyl or phenyl substituted with C$_{1-6}$alkyl, hydroxy, amino, C$_{1-6}$alkyloxy or halo; and Ar$^2$ is phenyl or phenyl substituted with C$_{1-6}$alkyl, hydroxy, amino, C$_{1-6}$alkyloxy or halo.

R$^4$ or R$^5$ may also be bound to one of the nitrogen atoms in the imidazole ring. In that case the hydrogen on the nitrogen is replaced by R$^4$ or R$^5$ and the meaning of R$^4$ and R$^5$ when bound to the nitrogen is limited to hydrogen, Ar$^1$, C$_{1-6}$alkyl, hydroxyC$_{1-6}$alkyl, C$_{1-6}$alkyloxyC$_{1-6}$alkyl, C$_{1-6}$alkyloxycarbonyl, C$_{1-6}$alkylS(O)C$_{1-6}$alkyl, C$_{1-6}$alkylS(O)$_2$C$_{1-6}$alkyl.

As used in the foregoing definitions and hereinafter halo defines fluoro, chloro, bromo and iodo; C$_{1-6}$alkyl defines straight and branched chained saturated hydrocarbon radicals having from 1 to 6 carbon atoms such as, for example, methyl, ethyl, propyl, butyl, pentyl, hexyl and the like; C$_{1-8}$alkyl encompasses the straight and branched chained saturated hydrocarbon radicals as defined in C$_{1-6}$alkyl as well as the higher homologues thereof containing 7 or 8 carbon atoms such as, for example heptyl or octyl; C$_{1-12}$alkyl again encompasses C$_{1-8}$alkyl and the higher homologues thereof containing 9 to 12 carbon atoms, such as, for example, nonyl, decyl, undecyl, dodecyl; C$_{1-16}$alkyl again encompasses C$_{1-12}$alkyl and the higher homologues thereof containing 13 to 16 carbon atoms, such as, for example, tridecyl, tetradecyl, pentedecyl and hexadecyl; C$_{2-6}$alkenyl defines straight and branched chain hydrocarbon radicals containing one double bond and having from 2 to 6 carbon atoms such as, for example, ethenyl, 2-propenyl, 3-butenyl, 2-pentenyl, 3-pentenyl, 3-methyl-2-butenyl, and the like; C$_{1-6}$alkanediyl defines bivalent straight and branched chained saturated hydrocarbon radicals having from 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof. The term "C(=O)" refers to a carbonyl group, "S(O)" refers to a sulfoxide and "S(O)$_2$" to a sulfon. The term "natural amino acid" refers to a natural amino acid that is bound via a covalent amide linkage formed by loss of a molecule of water between the carboxyl group of the amino acid and the amino group of the remainder of the molecule. Examples of natural amino acids are glycine, alanine, valine, leucine, isoleucine, methionine, proline, phenylanaline, tryptophan, serine, threonine, cysteine, tyrosine, asparagine, glutamine, aspartic acid, glutamic acid, lysine, arginine, histidine.

The pharmaceutically acceptable acid or base addition salts as mentioned hereinabove are meant to comprise the therapeutically active non-toxic acid and non-toxic base addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The compounds of formula (I) which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The terms acid or base addition salt also comprise the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

Whenever used hereinafter, the term "compounds of formula (I)" is meant to include also the pharmaceutically acceptable acid or base addition salts and all stereoisomeric forms.

Preferably the substituent $R^{18}$ is situated on the 5 or 7 position of the quinolinone moiety and substituent $R^{19}$ is situated on the 8 position when $R^{18}$ is on the 7-position.

Interesting compounds are these compounds of formula (I) wherein X is oxygen.

Also interesting compounds are these compounds of formula (I) wherein the dotted line represents a bond, so as to form a double bond.

Another group of interesting compounds are those compounds of formula (I) wherein $R^1$ is hydrogen, $C_{1-6}$alkyl, $C_{1-6}$alkyloxy$C_{1-6}$alkyl, di($C_{1-6}$alkyl)amino$C_{1-6}$alkyl, or a radical of formula —$Alk^1$—C(=O)—$R^9$, wherein $Alk^1$ is methylene and $R^9$ is $C_{1-8}$alkylamino substituted with $C_{1-6}$alkyloxycarbonyl.

Still another group of interesting compounds are those compounds of formula (I) wherein $R^3$ is hydrogen or halo; and $R^2$ is halo, $C_{1-6}$alkyl, $C_{2-6}$alkenyl, $C_{1-6}$alkyloxy, trihalomethoxy or hydroxy$C_{1-6}$alkyloxy.

A further group of interesting compounds are those compounds of formula (I) wherein $R^2$ and $R^3$ are on adjacent positions and taken together to form a bivalent radical of formula (a-1), (a-2) or (a-3).

A still further group of interesting compounds are those compounds of formula (I) wherein $R^5$ is hydrogen and $R^4$ is hydrogen or $C_{1-6}$alkyl.

Yet another group of interesting compounds are those compounds of formula (I) wherein $R^7$ is hydrogen; and $R^6$ is $C_{1-6}$alkyl or halo, preferably chloro, especially 4-chloro.

A particular group of compounds are those compounds of formula (I) wherein $R^8$ is hydrogen, hydroxy, halo$C_{1-6}$alkyl, hydroxy$C_{1-6}$alkyl, cyano$C_{1-6}$alkyl, $C_{1-6}$alkyloxycarbonyl$C_{1-6}$alkyl, imidazolyl, or a radical of formula —$NR^{11}R^{12}$ wherein $R^{11}$ is hydrogen or $C_{1-12}$alkyl and $R^{12}$ is hydrogen, $C_{1-6}$alkyl, $C_{1-6}$alkyloxy, hydroxy, $C_{1-6}$alkyloxy$C_{1-6}$alkylcarbonyl, or a radical of formula —$Alk^2$—$OR^{13}$ wherein $R^{13}$ is hydrogen or $C_{1-6}$alkyl.

Preferred compounds are those compounds wherein $R^1$ is hydrogen, $C_{1-6}$alkyl, $C_{1-6}$alkyloxy$C_{1-6}$alkyl, di($C_{1-6}$alkyl)amino$C_{1-6}$alkyl, or a radical of formula —$Alk^1$—C(=O)—$R^9$, wherein $Alk^1$ is methylene and $R^9$ is $C_{1-8}$alkylamino substituted with $C_{1-6}$alkyloxycarbonyl; $R^2$ is halo, $C_{1-6}$alkyl, $C_{2-6}$alkenyl, $C_{1-6}$alkyloxy, trihalomethoxy, hydroxy $C_{1-6}$alkyloxy or $Ar^1$; $R^3$ is hydrogen; $R^4$ is methyl bound to the nitrogen in 3-position of the imidazole; $R^5$ is hydrogen; $R^6$ is chloro; $R^7$ is hydrogen; $R^8$ is hydrogen, hydroxy, halo$C_{1-6}$alkyl, hydroxy$C_{1-6}$alkyl, cyano$C_{1-6}$alkyl, $C_{1-6}$alkyloxycarbonyl$C_{1-6}$alkyl, imidazolyl, or a radical of formula —$NR^{11}R^{12}$ wherein $R^{11}$ is hydrogen or $C_{1-12}$alkyl and $R^{12}$ is hydrogen, $C_{1-6}$alkyl, $C_{1-6}$alkyloxy, $C_{1-6}$alkyloxy$C_{1-6}$alkylcarbonyl, or a radical of formula —$Alk^2$—$OR^{13}$ wherein $R^{13}$ is $C_{1-6}$alkyl; $R^{17}$ is hydrogen and $R^{18}$ is hydrogen.

Most preferred compounds are
4-(3-chlorophenyl)-6-[(4-chlorophenyl)hydroxy(1-methyl-1H-imidazol-5-yl)methyl]-1-methyl-2(1H)-quinolinone,
6-[amino(4-chlorophenyl)-1-methyl-1H-imidazol-5-ylmethyl]-4-(3-chlorophenyl)-1-methyl-2(1H)-quinolinone;
6-[(4-chlorophenyl)hydroxy(1-methyl-1H-imidazol-5-yl)methyl]-4-(3-ethoxyphenyl)-1-methyl-2(1H)-quinolinone;
6-[(4-chlorophenyl)(1-methyl-1H-imidazol-5-yl)methyl]-4-(3-ethoxyphenyl)-1-methyl-2(1H)-quinolinone monohydrochloride.monohydrate;
6-[amino(4-chlorophenyl)(1-methyl-1H-imidazol-5-yl)methyl]-4-(3-ethoxyphenyl)-1-methyl-2(1H)-quinolinone,
6-amino(4-chlorophenyl)(1-methyl-1H-imidazol-5-yl)methyl]-1-methyl-4-(3-propylphenyl)-2(1H)-quinolinone; a stereoisomeric form thereof or a pharmaceutically acceptable acid or base addition salt; and
(B)-6-[amino(4-chlorophenyl)(1-methyl-1H-imidazol-5-yl)methyl]-4-(3-chlorophenyl)-1-methyl-2(1H)-quinolinone; or a pharmaceutically acceptable acid addition salt thereof.

The compounds of formula (I), wherein X is oxygen, said compounds being represented by formula (I-a), may be prepared by hydrolysing an intermediate ether of formula (II), wherein R is $C_{1-6}$alkyl, according to art-known methods, such as stirring the intermediate of formula (II) in an aqueous acid solution. An appropriate acid is for instance hydrochloric acid. Subsequently the resulting quinolinone wherein $R^1$ is hydrogen may be transformed into a quinolinone, wherein $R^1$ has a meaning as defined hereinabove apart from hydrogen, by art-known N-alkylation.

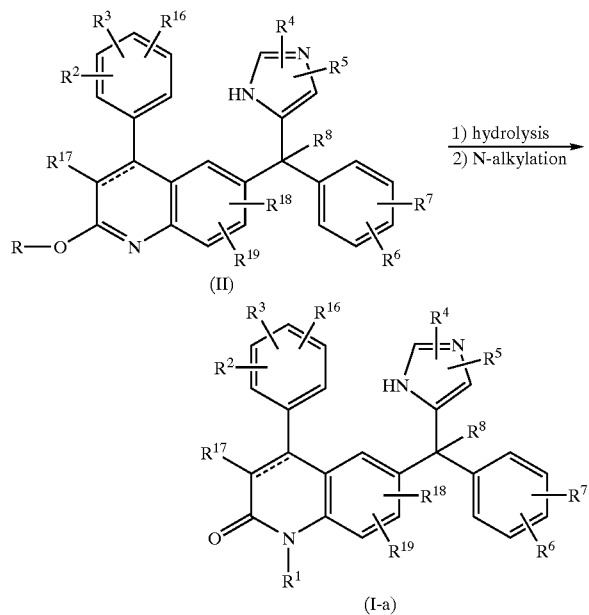

The compounds of formula (I), wherein $R^8$ is hydroxy, said compounds being referred to as compounds of formula (I-b) may be prepared by reacting an intermediate ketone of formula (III) with a intermediate of formula (IV-a), wherein P is an optional protective group such as, for example, a sulfonyl group, e.g. a dimethylamino sulfonyl group, which can be removed after the addition reaction. Said reaction requires the presence of a suitable strong base, such as, for example, butyl lithium in an appropriate solvent, such as, for example, tetrahydrofuran and the presence an appropriate silanederivative, such as, for example, triethylchlorosilane. During the work-up procedure an intermediate silane derivative is hydrolyzed. Other procedures with protective groups analogous to silanederivatives can also be applied.

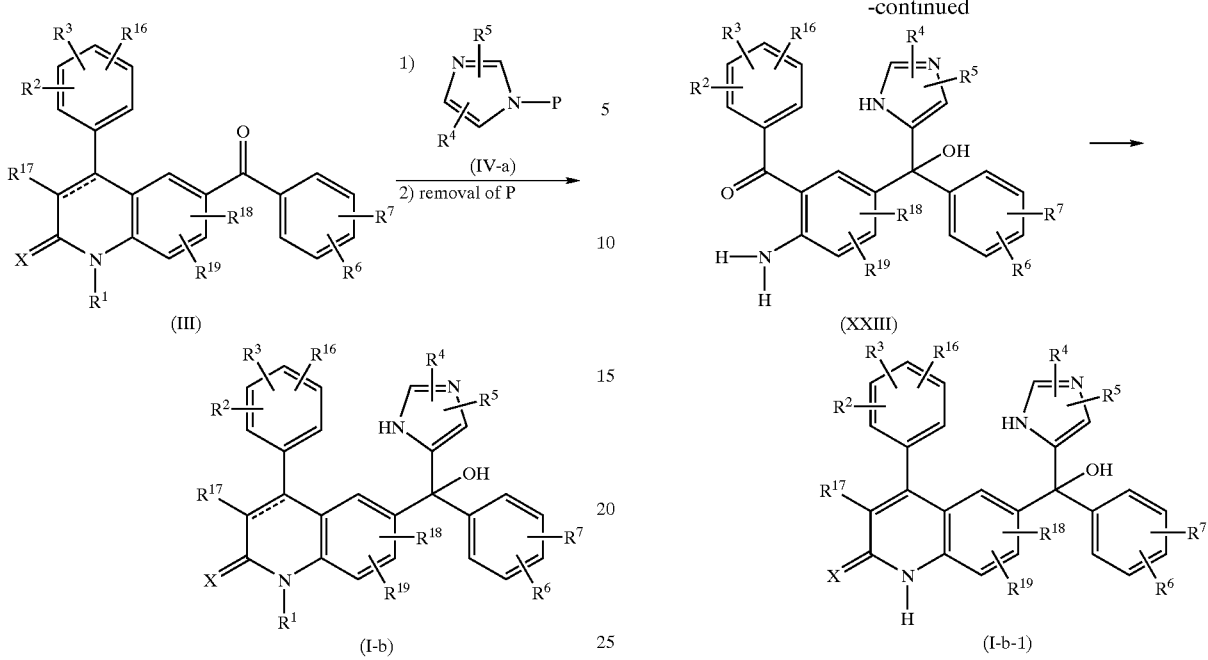

Compounds of formula (I-b-1), being compounds of formula (I-b) wherein the dotted line is a bond and $R^1$ is hydrogen, can be prepared by reacting an intermediate of formula (XXI) with an intermediate of formula (IV-a), as described hereinabove for the synthesis of compounds of formula (I-b). The thus obtained intermediate of formula (XXII) undergoes ring opening of the isoxazole moiety by stirring it with an acid, such as, e.g. $TiCl_3$, in the presence of water. Subsequent treatment of an intermediate of formula (XXIII) with a suitable reagent such as, e.g. $R^{17}CH_2COCl$ or $R^{17}CH_2COOC_2H_5$, yields either directly a compound of formula (I-b-1) or an intermediate which can be converted to a compound of formula (I-b-1) by treatment with a base such as, e.g. potassium tert-butoxide.

Intermediates of formula (XXI) can conveniently be prepared by treating an intermediate of formula (XVI), described hereinafter, under acidic conditions.

Compounds of formula (I) wherein $R^8$ is a radical of formula $-N-R^{11}R^{12}$, said compounds being represented by formula (I-g) may be prepared by reacting an intermediate of formula (XIII), wherein W is an appropriate leaving group such as, for example, halo, with a reagent of formula (XIV). Said reaction may be performed by stirring the reactants in an appropriate solvent such as, for example, tetrahydrofuran.

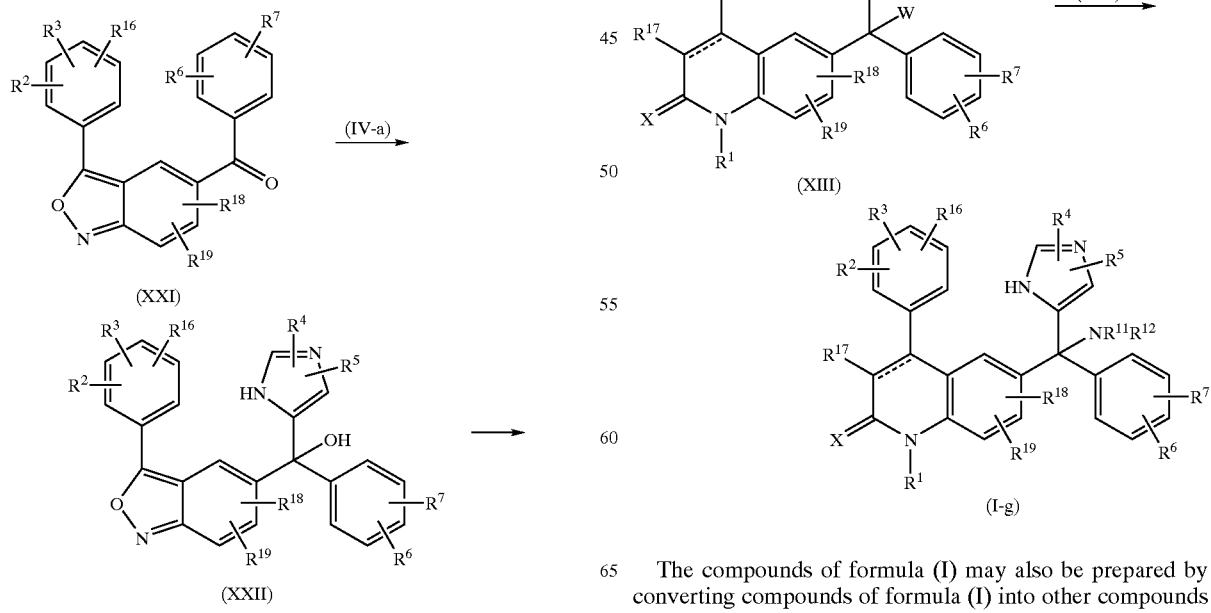

The compounds of formula (I) may also be prepared by converting compounds of formula (I) into other compounds of formula (I).

Compounds wherein the dotted line represents a bond can be converted into compounds wherein the dotted line does not represent a bond, by art-known hydrogenation methods. Vice versa, compounds wherein the dotted line does not represent a bond may be converted into compounds wherein the dotted line represents a bond by art-known oxidation reactions.

Compounds of formula (I) wherein $R^8$ is hydroxy, said compounds being represented by formula (I-b) may be converted into compounds of formula (I-c), wherein $R^{8a}$ has the meaning of $R^{10}$ except for hydrogen, by art-know O-alkylation or O-acylation reactions; such as, for instance, reacting the compound of formula (I-b) with an alkylating reagent such as $R^{8a}$—W in appropriate conditions, such as, for example, a dipolar aprotic solvent, e.g. DMF, in the presence of a base, e.g. sodium hydride. W is a suitable leaving group, such as, for example, halo or a sulfonylgroup.

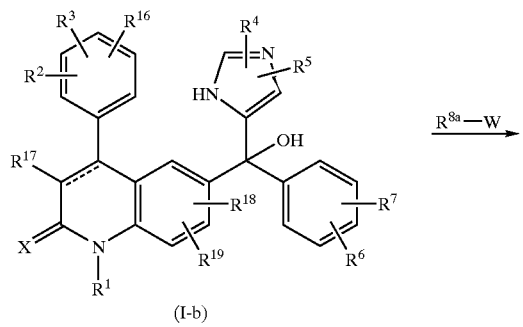

(I-b)

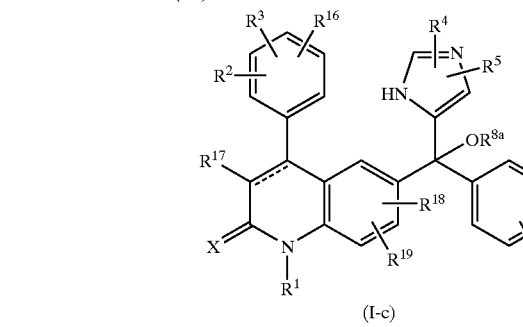

(I-c)

As an alternative to the above reaction procedure, compounds of formula (I-c) may also be prepared by reacting an intermediate of formula (I-b) with a reagent of formula $R^{8a}$—OH in acidic medium.

Compounds of formula (I-b) may also be converted into compounds of formula (I-g), wherein $R^{11}$ is hydrogen and $R^{12}$ is $C_{1-16}$alkylcarbonyl, by reacting compounds of formula (I-b) in acidic medium, such as sulfuric acid, with $C_{1-16}$alkyl-CN in a Ritter type reaction. Further, compounds of formula (I-b) may also be converted into compounds of formula (I-g), wherein $R^{11}$ and $R^{12}$ are hydrogen, by reacting compounds (I-b) with ammonium acetate and subsequent treatment with $NH_3$ (aq.).

Compounds of formula (I-b) may also be converted into compounds of formula (I-d), wherein $R^8$ is hydrogen, by submitting the compounds of formula (I-b) to appropriate reducing conditions, such as, stirring in trifluoroacetic acid in the presence of an appropriate reducing agent, such as sodium borohydride or alternatively stirring the compounds of formula (I-b) in acetic acid in the presence of form amide. Furthermore, compounds of formula (I-d) wherein $R^8$ is hydrogen may be converted into compounds of formula (I-e) wherein $R^{8b}$ is $C_{1-6}$alkyl by reacting compounds of formula (I-d) with a reagent of formula (V) in an appropriate solvent, such as, for instance, diglyme in the presence of a base such as, for example, potassium butoxide.

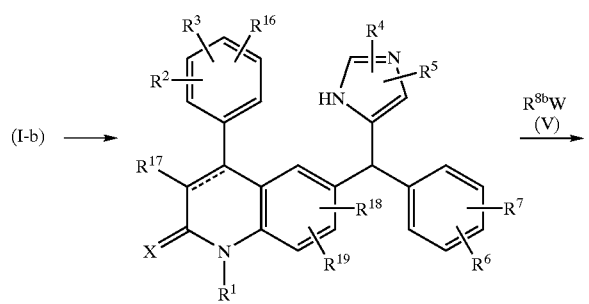

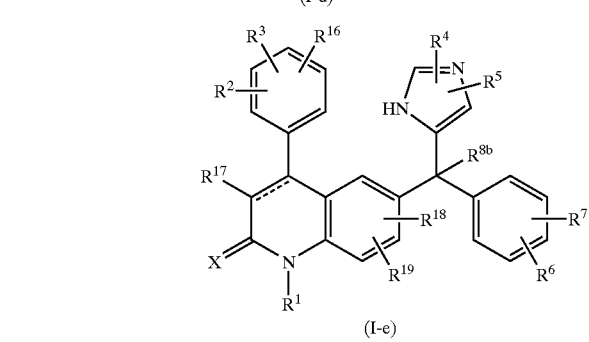

A compound of formula (I-f), defined as a compound of formula (I) wherein X is sulfur may be prepared by reacting the corresponding compound of formula (I-a), with a reagent like phosphorus pentasulfide or Lawesson's reagent in a suitable solvent such as, for example, pyridine.

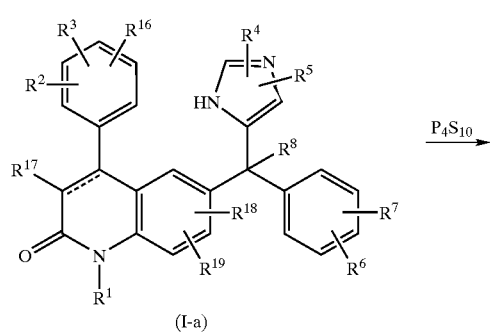

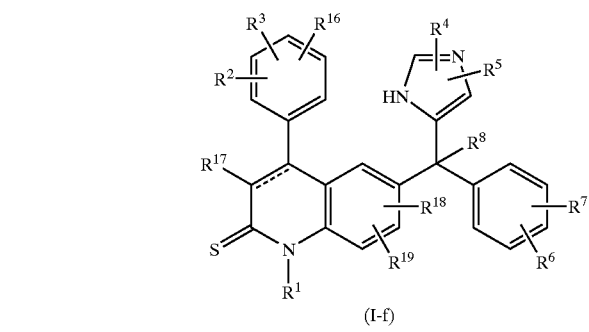

Compounds of formula of formula (I), wherein $R^1$ is hydrogen and X is oxygen, said compounds being defined as compounds of formula (I-a-1) may be prepared by reacting a nitrone of formula (VI) with the anhydride of a carboxylic acid, such as, for example, acetic anhydride, thus forming the corresponding ester on the 2 position of the quinoline moiety. Said quinoline ester can be hydrolyzed in situ to the corresponding quinolinone using a base such as, for example, potassium carbonate.

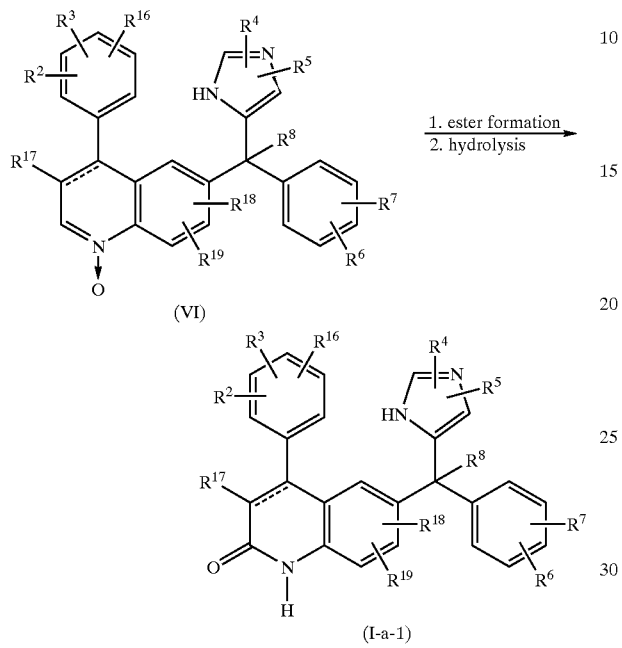

Alternatively, compounds of formula (I-a-1) can be prepared by reacting a nitrone of formula (VI) with a sulfonyl containing electrophilic reagent such as, for example, p-toluenesulfonylchloride in the presence of a base such as, for example, aqueous potassium carbonate. The reaction initially involves the formation of a 2-hydroxyquinoline derivative which is subsequently tautomerized to the desired quinolinone derivative. The application of art-known conditions of phase transfer catalysis may enhance the rate of the reaction.

Compounds of formula (I-a-1) may also be prepared by an intramolecular photochemical rearrangement of compounds of formula (VI). Said rearrangement can be carried out by dissolving the reagents in a reaction-inert solvent and irradiating at a wavelength of 366 nm. It is advantageous to use degassed solutions and to conduct the reaction under an inert atmosphere such as, for example, oxygen free argon or nitrogen gas, in order to minimize undesired side reactions or reduction of quantum yield.

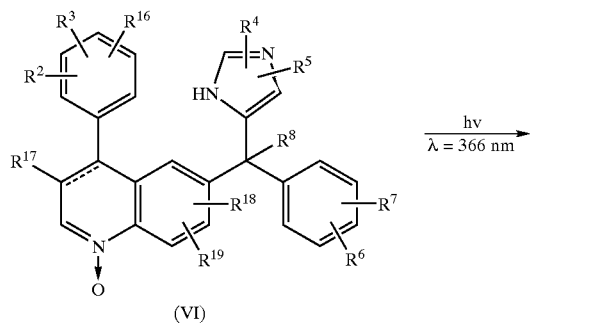

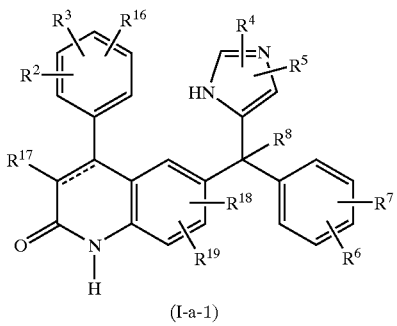

The compounds of formula (I) may also be converted into each other via art-known reactions or functional group transformations. A number of such transformations are already described hereinabove. Other examples are hydrolysis of carboxylic esters to the corresponding carboxylic acid or alcohol; hydrolysis of amides to the corresponding carboxylic acids or amines; hydrolysis of nitriles to the corresponding amides; amino groups on imidazole or phenyl may be replaced by a hydrogen by art-known diazotation reactions and subsequent replacement of the diazo-group by hydrogen; alcohols may be converted into esters and ethers; primary amines may be converted into secondary or tertiary amines; double bonds may be hydrogenated to the corresponding single bond.

Intermediates of formula (III) may be prepared by reacting a quinolinone derivative of formula (VIII) with an intermediate of formula (IX) or a functional derivative thereof under appropriate conditions, such as, for example, a strong acid, e.g. polyphosphoric acid in an appropriate solvent. The intermediate of formula (VIII) may be formed by cyclization of an intermediate of formula (VII) by stirring in the presence of a strong acid, e.g. polyphosphoric acid. Optionally said cyclization reaction may be followed by an oxidation step, which can be performed by stirring the intermediate formed after cyclization in an appropriate solvent, such as, for example, a halogenated aromatic solvent, e.g. bromobenzene, in the presence of a oxidizing agent, e.g. bromine or iodine. At this stage it may also be appropriate to change the $R^1$ substituent by art-known functional group transformation reaction.

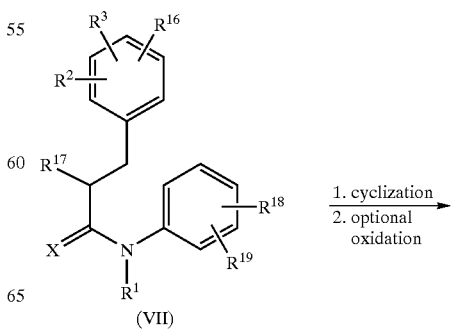

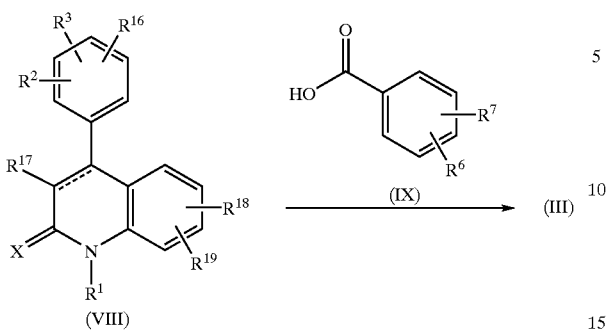

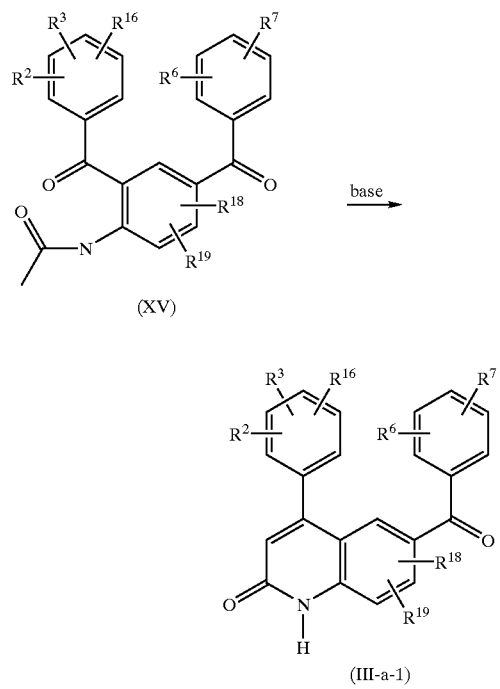

Intermediates of formula (III-a-1), being intermediates of formula (III) wherein the dotted line is a bond, $R^1$ and $R^{17}$ are hydrogen and X is oxygen, can be prepared starting from an intermediate of formula (XVII), which is conveniently prepared by protecting the corresponding ketone. Said intermediate of formula (XVII) is stirred with an intermediate of formula (XVIII) in the presence of a base such as sodium hydroxide, in an appropriate solvent, such as an alcohol, e.g. methanol. The thus obtained intermediate of formula (XVI) undergoes hydrolysis of the ketal and ring opening of the isoxazole moiety by stirring the intermediate of formula (XVI) with an acid, such as, for example, $TiCl_3$, in the presence of water. Subsequently acetic anhydride is used to prepare an intermediate of formula (XV), which undergoes ring closure in the presence of a base such as, for example, potassium tert-butoxide.

Intermediates of formula (III-a-1) can easily be converted to intermediates of formula (III-a), defined as intermediates of formula (III) wherein the dotted line represents a bond, X is oxygen, $R^{17}$ is hydrogen and $R^1$ is other than hydrogen, using art-known N-alkylation procedures.

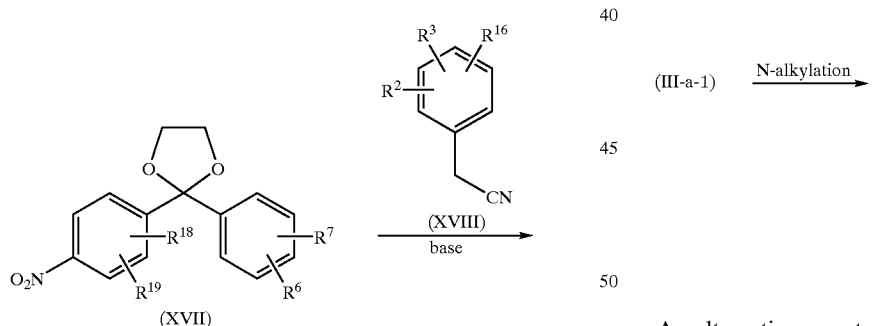

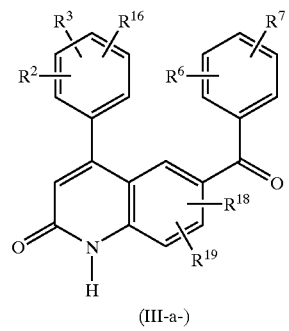

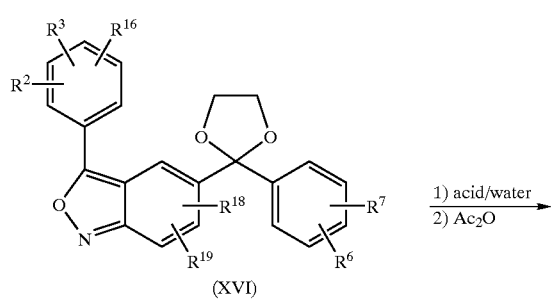

An alternative way to prepare intermediates of formula (III-a-1), wherein X is oxygen and $R^1$ is hydrogen, starts from an intermediate of formula (XVI), which is conveniently converted to intermediates of formula (XIX) using catalytic hydrogenation conditions, e.g. by using hydrogen gas and palladium on carbon in a reaction-inert solvent such as, e.g. tetrahydrofuran. Intermediates of formula (XIX) are converted to intermediates of formula (XX) by submitting intermediates (XIX) to an acetylation reaction, e.g. by treatment with the anhydride of a carboxylic acid, e.g. acetic anhydride in a reaction-inert solvent, e.g. toluene, and subsequent treatment with a base such as, e.g. potassium tert-butoxide in a reaction-inert solvent, e.g. 1,2- dimethoxyethane. Intermediates of formula (III-a-1) can be obtained by treating intermediates of formula (XX) in acidic conditions.

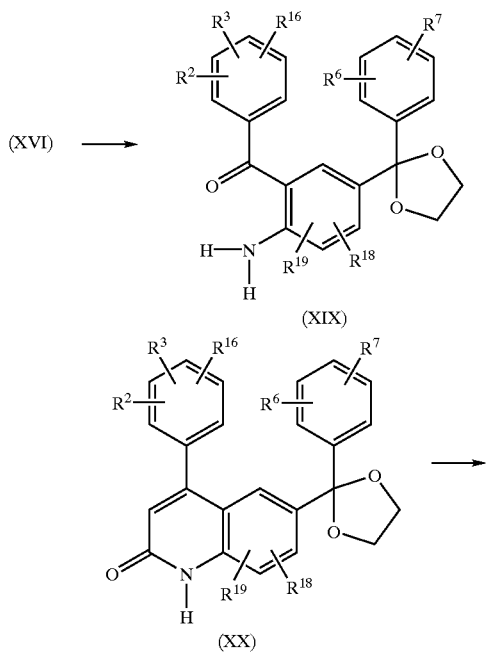

Intermediates of formula (II) may be prepared by reacting an intermediate of formula (X), wherein W is an appropriate leaving group, such as, for example, halo, with an intermediate ketone of formula (XI). This reaction is performed by converting the intermediate of formula (X) into a organometallic compound, by stirring it with a strong base such as butyl lithium and subsequently adding the intermediate ketone of formula (XI). Although this reaction gives at first instance a hydroxy derivative (i.e. $R^8$ is hydroxy), said hydroxy derivative can be converted into other intermediates wherein $R^8$ has another definition by performing art-known (functional group) transformations.

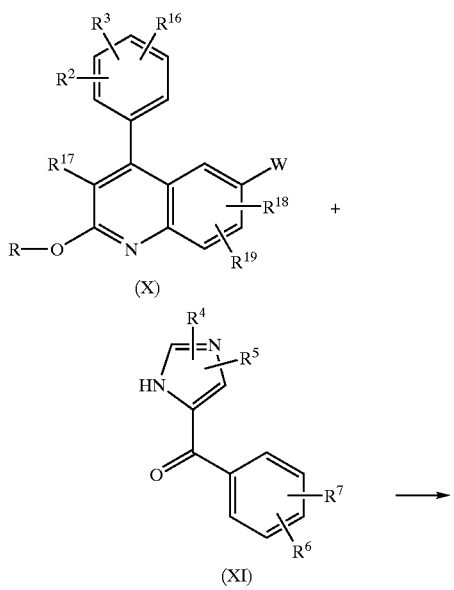

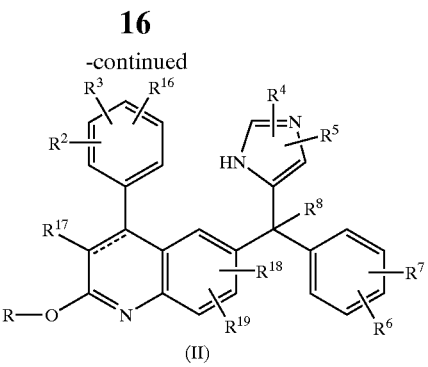

The intermediate nitrones of formula (VI) may be prepared by N-oxidizing quinoline derivatives of formula (XII) with an appropriate oxidizing agent such as, for example, chloro-peroxybenzoic acid or $H_2O_2$ in an appropriate solvent such as, for example, dichloromethane.

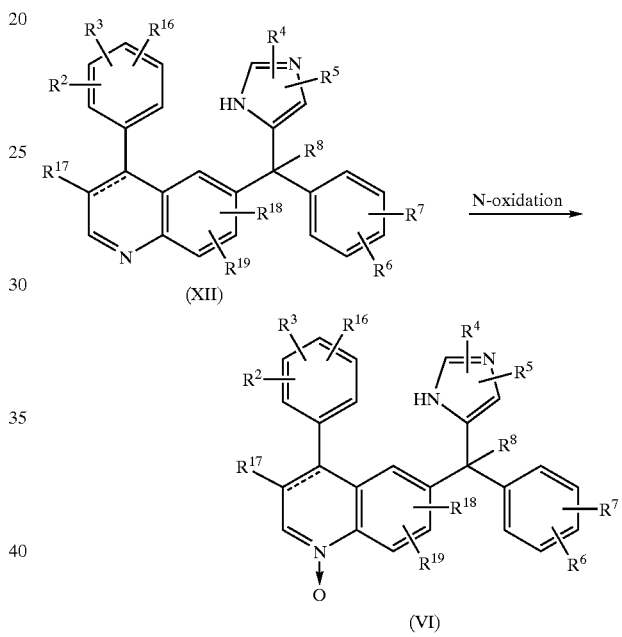

Said N-oxidation may also be carried out on a precursor of a quinoline of formula (XII).

The intermediates of formula (XII) are supposed to be metabolized in vivo into compounds of formula (I) via intermediates of formula (VI). Hence, intermediates of formula (XII) and (VI) may act as prodrugs of compounds of formula (I).

The compounds of formula (I) and some of the intermediates have at least one stereogenic center in their structure. This stereogenic center may be present in a R or a S configuration.

The compounds of formula (I) as prepared in the hereinabove described processes are generally racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

This invention provides a method for inhibiting the abnormal growth of cells, including transformed cells, by administering an effective amount of a compound of the invention. Abnormal growth of cells refers to cell growth independent of normal regulatory mechanisms (e.g. loss of contact inhibition). This includes the abnormal growth of: (1) tumor cells (tumors) expressing an activated ras oncogene; (2) tumor cells in which the ras protein is activated as a result of oncogenic mutation of another gene; (3) benign and malignant cells of other proliferative diseases in which aberrant ras activation occurs. Furthermore, it has been suggested in literature that ras oncogenes not only contribute to the growth of of tumors in vivo by a direct effect on tumor cell growth but also indirectly, i.e. by facilitating tumor-induced angiogenesis (Rak. J. et al, *Cancer Research*, 55, 4575–4580, 1995). Hence, pharmacologically targetting mutant ras oncogenes could conceivably suppress solid tumor growth in vivo, in part, by inhibiting tumor-induced angiogenesis.

This invention also provides a method for inhibiting tumor growth by administering an effective amount of a compound of the present invention, to a subject, e.g. a mammal (and more particularly a human) in need of such treatment. In particular, this invention provides a method for inhibiting the growth of tumors expressing an activated ras oncogene by the administration of an effective amount of the compounds of the present invention. Examples of tumors which may be inhibited, but are not limited to, lung cancer (e.g. adenocarcinoma), pancreatic cancers (e.g. pancreatic carcinoma such as, for example exocrine pancreatic carcinoma), colon cancers (e.g. colorectal carcinomas, such as, for example, colon adenocarcinoma and colon adenoma), hematopoietic tumors of lymphoid lineage (e.g. acute lymphocytic leukemia, B-cell lymphoma, Burkitt's lymphoma), myeloid leukemias (for example, acute myelogenous leukemia (AML)), thyroid follicular cancer, myelodysplastic syndrome (MDS), tumors of mesenchymal origin (e.g. fibrosarcomas and rhabdomyosarcomas), melanomas, teratocarcinomas, neuroblastomas, gliomas, benign tumor of the skin (e.g. keratoacanthomas), breast carcinoma, kidney carninoma, ovary carcinoma, bladder carcinoma and epidermal carcinoma.

This invention may also provide a method for inhibiting proliferative diseases, both benign and malignant, wherein ras proteins are aberrantly activated as a result of oncogenic mutation in genes, i.e. the ras gene itself is not activated by mutation to an oncogenic mutation to an oncogenic form, with said inhibition being accomplished by the administration of an effective amount of the compounds described herein, to a subject in need of such a treatment. For example, the benign proliferative disorder neurofibromatosis, or tumors in which ras is activated due to mutation or overexpression of tyrosine kinase oncogenes may be inhibited by the compounds of this invention.

Hence, the present invention discloses the compounds of formula (I) for use as a medicine as well as the use of these compounds of formula (I) for the manufacture of a medicament for treating one or more of the above mentioned conditions.

Some of the intermediates of formula (XIII), wherein W is halo may also show farnesyl protein transferase inhibiting activity.

In view of their useful pharmacological properties, the subject compounds may be formulated into various pharmaceutical forms for administration purposes. To prepare the pharmaceutical compositions of this invention, an effective amount of a particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs; and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Those skilled in the art could easily determine the effective amount from the test results presented hereinafter. In general it is contemplated that an effective amount would be from 0.0001 mg/kg to 100 mg/kg body weight, and in particular from 0.001 mg/kg to 10 mg/kg body weight. It may be appropriate to administer the required dose as two, three, four or more sub-doses at appropriate intervals throughout the day. Said sub-doses may be formulated as unit dosage forms, for example, containing 0.01 to 500 mg, and in particular 0.1 mg to 200 mg of active ingredient per unit dosage form.

EXPERIMENTAL PART

Hereinafter "THF" means tetrahydrofuran, "DIPE" means diisopropylether, "DCM" means dichloromethane, "DMF" means N,N-dimethylformamide and "ACN" means acetonitrile. Of some compounds of formula (I) the absolute stereochemical configuration was not experimentally determined. In those cases the stereochemically isomeric form which was first isolated is designated as "A" and the second as "B", without further reference to the actual stereochemical configuration.

A. Preparation of the Intermediates

Example A.1

1a) N-Phenyl-3-(3-chlorophenyl)-2-propenamide (58.6 g) and polyphosphoric acid (580 g) were stirred at 100° C. overnight. The product was used without further purification, yielding quant. (±)-4-(3-chlorophenyl)-3,4-dihydro-2(1H)-quinolinone (interm. 1-a).

1b) Intermediate (1-a) (58.6 g), 4-chlorobenzoic acid (71.2 g) and polyphosphoric acid (580 g) were stirred at 140° C. for 48 hours. The mixture was poured into ice water and filtered off. The precipitate was washed with water, then with a diluted $NH_4OH$ solution and taken up in DCM. The organic layer was dried ($MgSO_4$), filtered off and evaporated. The residue was purified by column chromatography over silica gel (eluent: $CH_2Cl_2/CH_3OH/NH_4OH$ 99/1/0.1). The pure fractions were collected and evaporated, and recrystallized from $CH_2Cl_2/CH_3OH/DIPE$, yielding 2.2g of (±)-6-(4-chlorobenzoyl)-4-(3-chlorophenyl)-3,4-dihydro-2 (1H)-quinolinone (interm. 1-b, mp. 194.8° C.).

1c) Bromine (3.4 ml) in bromobenzene (80 ml) was added dropwise at room temperature to a solution of intermediate (I-b) (26 g) in bromobenzene (250 ml) and the mixture was stirred at 160° C. overnight. The mixture was cooled to room temperature and basified with $NH_4OH$. The mixture was evaporated, the residue was taken up in ACN and filtered off. The precipitate was washed with water and air dried, yielding 24 g (92.7%) of product. A sample was recrystallized from $CH_2Cl_2/CH_3OH/DIPE$, yielding 2.8 g of 6-(4-chlorobenzoyl)-4-(3-chlorophenyl)-2(1H)-quinolinone; mp. 234.8° C. (interm. 1-c).

1d) Iodomethane (6.2 ml) was added to a mixture of intermediate (1-c) (20 g) and benzyltriethylammonium chloride (5.7 g) in tetrahydrofuran (200 ml) and sodium hydroxide (10N) (200 ml) and the mixture was stirred at room temperature overnight, ethyl acetate was added and the mixture was decanted. The organic layer was washed with water, dried ($MgSO_4$), filtered off and evaporated till dryness. The residue was purified by column chromatography over silica gel (eluent: $CH_2Cl_2/CH_3OOH/NH_4OH$ 99.75/0.25/0.1). The pure fractions were collected and evaporated, yielding 12.3 g (75%) of 6-(4-chlorobenzoyl)-4-(3-chlorophenyl)-1-methyl-2(1H)-quinolinone; mp. 154.7° C. (interm. 1-d).

In a similar way, but starting from intermediate (1-b), (±)-6-(4-chlorobenzoyl)-4-(3-chlorophenyl)-3,4-dihydro-1-methyl-2(1H)-quinolinone (interm 1-e) was prepared.

Example A.2

Butyllithium in hexane (1.6 M) (12.75 ml) was added dropwise at −20° C. under $N_2$ to a solution of 6-bromo-4-(3-chlorophenyl)-2-methoxyquinoline (6.7 g) in THF (60 ml) and the mixture was stirred at −20° C. for 30 minutes. A solution of (1-butyl-1H-imidazol-5-yl)(4-chlorophenyl) methanone (3.35 g) in tetrahydrofuran (30 ml) was added at −20° C. under $N_2$ and the mixture was stirred at room temperature for one night. Water was added and the mixture was extracted with ethyl acetate. The organic layer was dried ($MgSO_4$), filtered off and evaporated. The residue was purified by column chromatography over silica gel (eluent: $CH_2Cl_2/CH_3OH/NH_4OH$ 97/3/0.1). The pure fractions were collected and evaporated, yielding 2.5 g (total 48%) of (±)-α-(1-butyl-1H-imidazol-5-yl)-4-(3-chlorophenyl)-α-(4-chlorophenyl)-2-methoxy-6-quinolinemethanol (interm. 2).

Example A.3

3a) Butyllithium (30.1 ml) was added slowly at −78° C. to a solution of N,N-dimethyl-1H-imidazol-1-sulfonamide (8,4 g) in tetrahydrofuran (150 ml) and the mixture was stirred at −78° C. for 15 minutes. Chlorotriethylsilane (8.1 ml) was added and the mixture was stirred till the temperature reached 20° C. The mixture was cooled till −78° C., butyllithium (30.1 ml) was added, the mixture was stirred at −78° C. for 1 hour and allowed to reach −15° C. The mixture was cooled again till −78° C., a solution of 6-(4-chlorobenzoyl)-1-methyl-4-phenyl-2(1H)-quinolinone (15 g) in tetrahydrofuran (30 ml) was added and the mixture was stirred till the temperature reached 20° C. The mixture was hydrolized and extracted with ethyl acetate. The organic layer was dried ($MgSO_4$), filtered off and evaporated till dryness. The product was used without further purification, yielding 26 g (100%) of (±)-4-[(4-chlorophenyl)(1,2-dihydro-1-methyl-2-oxo-4-phenyl-6-quinolinyl) hydroxymethyl]-N,N-dimethyl-2-(triethylsilyl)-1H-imidazole-1-sulfonamide (interm. 3-a).

A mixture of intermediate (3-a) (26 g) in sulfuric acid (2.5 ml) and water (250 ml) was stirred and heated at 110° C. for 2 hours. The mixture was poured into ice, basified with $NH_4OH$ and extracted with DCM. The organic layer was dried ($MgSO_4$), filtered off and evaporated till dryness. The residue was purified by column chromatography over silica gel (eluent: $CH_2Cl_2/CH_3OH/NH_4OH$ 99/1/0.2). The pure fractions were collected and evaporated, yielding 2.4 g (11%) of (±)-4-[(4-chlorophenyl)(1,2-dihydro-1-methyl-2-oxo-4-phenyl-6-quinolinyl)hydroxymethyl]-N,N-dimethyl-1H-imidazole-1-sulfonamide (interm. 3-b).

Example A.4

Compound (3) (3 g) was added at room temperature to thionyl chloride (25 ml). The mixture was stirred and refluxed at 40° C. overnight. The solvent was evaporated till dryness. The product was used without further purification, yielding 3.49 g of (±)-4-(3-chlorophenyl)-1-methyl-6-[1-(4-methylphenyl)-1-(4-methyl-4-pyrrol-3-yl)ethyl]-2(1H)-quinolinone hydrochloride (interm. 4).

Example A.5 a) Toluene (1900 ml) was stirred in a round-bottom flask (5 l) using a water separator. (4-Chlorophenyl)(4-nitrophenyl)methanone (250 g) was added portionwise. p-Toluene-sulfonic acid (54.5 g) was added portionwise. Ethylene glycol (237.5 g) was poured out into the mixture. The mixture was stirred and refluxed for 48 hours. The solvent was evaporated. The residue was dissolved into ethyl acetate (5 l) and washed twice with a $K_2CO_3$ 10% solution. The organic layer was separated, dried ($MgSO_4$), filtered and the solvent was evaporated. The residue was stirred in DIPE, filtered off and dried (vacuum, 40° C., 24 hours), yielding 265 g (91%) of 2-(4-chlorophenyl)-2-(4-nitrophenyl)-1,3-dioxolane (interm. 5-a).

b) Sodium hydroxide (16.4 g) and (3-methoxyphenyl) acetonitrile (20.6 ml) were added at room temperature to a solution of interm. (5-a) (25 g) in methanol (100 ml) and the mixture was stirred at room temperature overnight. Water was added, the precipitate was filtered off, washed with cold methanol and dried. The product was used without further purification, yielding 30 g (90%) of 5-[2-(4-chlorophenyl)-1,3-dioxolan-2-yl]-3-(3-methoxyphenyl)-2,1-benzisoxazole (interm. 5-b).

c) Interm. (5-b) (30 g) in THF (250 ml) was hydrogenated with palladium on carbon (3 g) as a catalyst at room temperature for 12 hours under a 2.6 $10^5$ Pa pressure in a Parr apparatus. After uptake of $H_2$ (1 equivalent), the catalyst was filtered through celite and the filtrate was evaporated till dryness. The product was used without further purification, yielding 31.2g (100%) of (3-methoxyphenyl)[2-amino-5-[2-(4-chlorophenyl)-1,3-dioxolan-2-yl]phenyl]methanone (interm. 5-c).

d) Acetic anhydride (13.9 ml) was added to a solution of interm. (5-c) (31.2 g) in toluene (300 ml) and the mixture was stirred and refluxed for 2 hours. The mixture was evaporated till dryness and the product was used without further purification, yielding 36.4 g (100%) of N-[2-(3-methoxybenzoyl)-4-[2-(4-chlorophenyl)-1,3-dioxolan-2-yl] phenyl]acetamide (interm. 5-d).

e) Potassium tert-butoxide (33 g) was added portionwise at room temperature to a solution of interm. (5-d) (36.4 g) in 1,2-dimethoxyethane (350 ml) and the mixture was stirred at room temperature overnight. The mixture was hydrolized and extracted with DCM. The organic layer was dried ($MgSO_4$), filtered off and evaporated till dryness. The product was used without further purification, yielding 43 g of 6-[2-(4-chlorophenyl)-1,3-dioxolan-2-yl]-4-(3-methoxyphenyl)-2(1H)-quinolinone (interm. 5-e).

f) A mixture of interm. (5-e) (43 g) in HCl (3N, 400 ml) and methanol (150 ml) was stirred and refluxed overnight. The mixture was cooled and filtered off. The precipitate was washed with water and diethyl ether and dried. The product was used without further purification, yielding 27g (94%) of 6-(4-chlorobenzoyl)-4-(3-methoxyphenyl)-2(1H)-quinolinone (interm. 5-f).

g) Methyl iodide (1.58 ml) was added to a solution of interm. (5-f) (7.6 g) and benzyltriethylammonium chloride (BTEAC) (2.23 g) in THF (80 ml) and sodium hydroxide (40%, 80 ml). The mixture was stirred at room temperature for 2 hours. Water was added and the mixture was extracted with ethyl acetate. The organic layer was dried ($MgSO_4$), filtered, and the solvent was evaporated. The residue was purified by flash column chromatography over silica gel (eluent: DCM 100%). The desired fractions were collected and the solvent was evaporated, yielding 7.1g (90%) of 6-(4-chlorobenzoyl)-4-(3-methoxyphenyl)-1-methyl-2(1H)-quinolinone (interm. 5-g).

Example A.6 a) 3-(3-Chlorophenyl)-5-[2-(4-chlorophenyl)-1,3-dioxolan-2-yl]-2,1-benzisoxazole (interm. 6-a) was prepared analogous as intermediate (5-b).

b) A mixture of intermediate (6-a) (30 g) in HCl 3 N (220 ml) and methanol (165 ml) was stirred at 100° C. for 5 hours. The mixture was poured into ice and basified with $NH_3$ (aq.). The precipitate was filtered off, washed with water and diethyl ether and dried, yielding 24.9 g (93%) of (4-chlorophenyl)[3-(3-chlorophenyl)-2,1-benzisoxazol-5-yl]methanone (interm. 6-b). The product was used without further purification.

c) Butyllithium in hexanes (10 ml) was added slowly at −70° C. under $N_2$ flow to a solution of 1-methylimidazole (1.31 g) in THF (30 ml). The mixture was stirred at −70° C. for 45 minutes. Chlorotriethylsilane (2.7 ml) was added. The mixture was allowed to warm to 15° C. and cooled to −70° C. Butyllithium (10 ml) was added slowly. The mixture was stirred at −70° C. for 1 hour, allowed to warm to −15° C. and cooled to −70° C. A solution of intermediate (6-b) (4.9 g) in THF (60 ml) was added. The mixture was stirred at −70° C. for 30 minutes, then hydrolyzed with water, extracted with ethyl acetate and decanted. The organic layer was dried ($MgSO_4$), filtered and the solvent was evaporated. The residue (8.2 g) was purified by column chromatography over silica gel (eluent: $CH_2Cl_2/CH_3OH/NH_4OH$ 96/4/0.2) and crystallized from 2-propanone/diethyl ether. The precipitate was filtered off and dried, yielding 1.5 g (25%) of (±)-3-(3-chlorophenyl)-α-(4-chlorophenyl)-α-(1-methyl-1H-imidazol-5-yl)-2,1-benzisoxazole-5-methanol (interm. 6-c).

d) $TiCl_3/15\%$ in $H_2O$ (200 ml) was added at room temperature to a solution of intermediate (6-c) (38 g) in THF (300 ml). The mixture was stirred at room temperature for 90 minutes. The mixture was poured out on ice, basified with $K_2CO_3$, filtered over celite, washed with ethyl acetate and decanted. The organic layer was dried ($MgSO_4$), filtered and the solvent was evaporated. The residue was purified by column chromatography over silica gel (eluent: $CH_2Cl_2/CH_3OH/NH_4OH$ 97/3/0.1 and 95/5/0.1), yielding 18.7 g (49%) of (±)-[2-amino-5-[(4-chlorophenyl)hydroxy(1-methyl-1H-imidazol-5-yl)methyl]phenyl](3-chlorophenyl) methanone (intern. 6-d).

B. Preparation of the Final Compounds

Example B.1

1-Methylimidazole (4.69 ml) in tetrahydrofuran (100 ml) was stirred at −78° C. A solution of butyllithium in hexanes (2.5 M) (36.7 ml) was added dropwise and the mixture was stirred at −78° C. for 15 minutes. Chlorotriethylsilane (9.87 ml) was added and the mixture was brought to room temperature. The mixture was cooled till −78° C., a solution of butyllithium in hexanes (2.5 M) (36.7 ml) was added dropwise, the mixture was stirred at −78° C. for 1 hour and brought till −15° C. The mixture was cooled till −78° C., a solution of intermediate (1-d) (20 g) in THF (40 ml) was added and the mixture was brought to room temperature. The mixture was hydrolized at 0° C. and extracted with ethyl acetate. The organic layer was dried ($MgSO_4$), filtered off and evaporated till dryness, yielding 36 g of product. The product was purified by column chromatography over silica gel (eluent: $CH_2Cl_2/CH_3OH/NH_4OH$ 97/3/0.1). The pure fractions were collected, evaporated, and crystallized from 2-propanone, $CH_3OH$ and $(C_2H_5)_2O$. The precipitate was filtered off, washed with $(C_2H_5)_2O$ and dried, yielding 12.4 g (52%) of (±)-4-(3-chlorophenyl)-6-[(4-chlorophenyl) hydroxy(1-methyl-1H-imidazol-5-yl)methyl]-1-methyl-2 (1H)-quinolinone; (comp. 3, mp.233.6° C.).

In a similar way, but using intermediate (5-g) or intermediate (I-e) instead of intermediate (1-d), respectively (±)-6-[(4-chlorophenyl)hydroxy(1-methyl-1H-imidazol-5-yl) methyl]-4-(3-methoxyphenyl)-1-methyl-2(1H)-quinolinone (comp. 36) and (±)-4-(3-chlorophenyl)-6-[(4-chlorophenyl) hydroxy(1-methyl-1H-imidazol-5-yl)methyl)-3,4-dihydro-1-methyl-2(1l)-quinolinone (comp. 127) were prepared.

Example B.2

Hydrochloric acid (60 ml) was added to a solution of intermediate (2) (2.5 g) in THF (10 ml) and the mixture was stirred and heated at 100° C. for 3 hours. The mixture was cooled, the precipitate was filtered off, washed with water, then with diethyl ether and dried, yielding 2.7 g (100%) of (±)-6-[(1-butyl-1H-imidazol-5-yl)-(4-chlorophenyl) hydroxymethyl]-4-(3-chlorophenyl)-2(1H)quinolinone (comp. 8).

Example B.3

Sodium hydride (0.28 g) was added to a mixture of compound (3) (3 g) in DMF (50 ml) under $N_2$ and the mixture was stirred for 15 minutes. Iodomethane (1.5 ml) was added and the mixture was stirred at room temperature for 1 hour. The mixture was hydrolized and extracted with diethyl ether and methanol. The organic layer was dried ($MgSO_4$), filtered off and evaporated till dryness, yielding 4.4 g of residue. The residue was purified by column chromatography over silica gel (eluent: $CH_2Cl_2/CH_3OH/NH_4OH$ 95.5/4.5/0.2). The pure fractions were collected and evaporated. The product was converted into the ethanedioic acid salt (1:1) in 2-propanone and filtered off. The residue was crystallized from 2-propanone, diethyl ether and DIPE. The precipitate was filtered off, washed with diethyl ether, dried and recrystallized from 2-propanone, methanol and DIPE. The precipitate was filtered off, washed with diethyl ether and dried, yielding 0.95 g (25%) of (±)-4-(3-chlorophenyl)-6-[(4-chlorophenyl)methoxy(1-methyl-1H-imidazol-5-yl)methyl]-1-methyl-2(1H)-quinolinone ethanedioate(1:1 ).dihydrate; (comp. 4, mp. 154.6° C.).

Example B.4

Iodomethane (0.38 ml) was added dropwise at room temperature to a solution of compound (8) (2.44 g) and N,N,N-triethylbenzenemethanaminium chloride (0.54 g) in tetrahydrofuran (30 ml) and sodium hydroxide (40%) (30 ml) and the mixture was stirred at room temperature for 3 hours. Water was added and the mixture was extracted with ethyl acetate. The organic layer was dried ($MgSO_4$), filtered off and evaporated. The residue was purified by column chromatography over silica gel (eluent: $CH_2Cl_2/CH_3OH/NH_4OH$ 96.5/3.5/0.1). The pure fractions were collected, evaporated and crystallized from 2-propanone and DIPE. The precipitate was filtered off, washed with diethyl ether and dried, yielding 1.4 g (56%) of (±)-4-(3-chlorophenyl)-6-[(1-butyl-1H-imidazol-5-yl)(4-chlorophenyl) hydroxymethyl]-1-methyl-2(1H)-quinolinone; (comp. 9, mp. 174.6° C.).

Example B.5

Iodomethane (1.4 ml) was added to a mixture of (±)-6-[(4-chlorophenyl)- 1H-imidazol-4-ylmethyl]-1-methyl-4-phenyl-2(1H)-quinolinone (7.5 g) and benzyltriethylammonium chloride (2 g) in THF (75 ml) and sodium hydroxide (75 ml) and the mixture was stirred at room temperature for 1 hour. Water was added and the mixture was extracted with ethyl acetate. The organic layer was dried ($MgSO_4$), filtered off and evaporated till dryness. The residue was purified by column chromatography over silica gel (eluent: $CH_2Cl_2/CH_3OH/NH_4OH$ 98.5/1.5/0.1). The pure fractions were collected and evaporated. Fraction 1 (3.5 g) was recrystallized from diethyl ether, yielding 3.3 g (42%) of (±)-6-[(4-chlorophenyl)(1-methyl-1H-imidazol-4-yl)methyl]-1-methyl-4-phenyl-2(1H)-quinolinone; mp. 149.9° C. (comp. 44). Fraction 2 was recrystallized from 2-propanone, methanol and diethyl ether, yielding 1.6 g (20%) of (±)-6-[(4chlorophenyl)(1-methyl-1H-imidazol-5-yl)methyl]-1-methyl-4-phenyl-2(1H)-quinolinone (comp. 2, mp. 96.8° C.).

Example B.6

Sodium borohydride (5.6 g) was added portionwise at 0° C. under $N_2$ to compound (3) (7.2 g) dissolved in trifluoroacetic acid (150 ml) and the mixture was stirred at room temperature overnight. The mixture was poured into ice, basified with NaOH 3N, then concentrated NaOH and extracted with ethyl acetate. The organic layer was dried ($MgSO_4$), filtered off and evaporated till dryness. The residue was purified by column chromatography over silica gel (eluent: $CH_2Cl_2/CH_3OH$ 95/5). The pure fractions were collected and evaporated, yielding 4.3 g (62%) of fraction 1; 0.2 g (3%) of fraction 2 and 2 g (29%) of fraction 3. Fraction 1 was converted into the ethanedioic acid salt (1:1) in 2-propanone and diethyl ether. The precipitate was filtered off, washed with diethyl ether and dried, yielding 4.7 g (55%) of (±)-4-(3-chlorophenyl)-6-[(4-chlorophenyl)(1-methyl-1H-imidazol-5-yl)methyl]-1-methyl-2(1H)-quinolinone ethanedioate(1:1).mono-hydrate (comp. 5, mp. 157.4° C.).

Example B.7

A solution of compound 90 (4.2 g) in 1,2-dimethoxyethane (70 ml) was stirred under $N_2$ for 30 minutes. Iodomethane (0.83 ml), followed by potassium tert-butoxide (2 g) were added portionwise and the mixture was stirred at room temperature for 30 minutes. Water was added and the mixture was extracted with ethyl acetate. The organic layer was dried ($MgSO_4$), filtered off and evaporated. The residue was purified by column chromatography over silica gel (eluent: cyclohexane/2-propanol/$NH_4OH$ 85/5/0.5 to 80/20/1) and converted into the ethanedioic acid salt, crystallized from 2-propanone and filtered off, yielding 1.16 g (23.6%) of (±)-4-(3-chlorophenyl)-6-[1-(4-chlorophenyl)-1-(1-methyl-1H-imidazol-5-yl)ethyl]-1-methyl-2(1H)-quinolinone.ethanedioate (1:1); (comp. 12, mp. 203.9° C.).

In a similar way, but replacing iodomethane by dichloromethane or dibromomethane, respectively (±)-6-[2-chloro-1-(4-chlorophenyl)-1-(1-methyl-1H-imidazol-5-yl) ethyl]-4-(3-chlorophenyl)-1-methyl-2(1H)-quinolinone ethanedioate (1:1) (comp. 69) and (±)-6-[2-bromo-1-(4-chlorophenyl)-1-(1-methyl-1H-imidazol-5-yl)ethyl]-4-(3-chlorophenyl)-1-methyl-2(1H)-quinolinone (comp. 70) were prepared.

Example B.8 a) Compound (3) (3 g) was separated (into its enantiomers) and purified by high-performance liquid chromatography over Chiracel OD (20 μm; eluent: hexane/ethanol 50/50). The pure (A)-fractions were collected, and the solvent was evaporated, yielding 1.6 g ((A); LCI:>99%). The pure (B)-fractions were collected, and the solvent was evaporated, yielding 1.5 g ((B); LCI:>99%). The (A)-residue was dissolved in 2-propanol and converted into the ethanedioic acid salt (1:1). The precipitate was filtered off and dried, yielding 0.6 g (17%) of (A)-4-(3-chlorophenyl)-6-[(4-chlorophenyl)-hydroxy(1-methyl-1H-imidazol-5-yl) methyl]-1-methyl-2(1H)-quinolinone ethanedioate (1:1); $[\alpha]_D^{20}$ =+17.96° (c=1% in methanol) (comp. 23). The (B)-residue was dissolved in 2-propanol and converted into the ethanedioic acid salt (1:1). The precipitate was filtered off and dried, yielding 0.6 g (17%) (B)-4-(3-chlorophenyl)-6-[(4-chlorophenyl)hydroxy(1-methyl-1H-imidazol-5-yl) methyl]-1-methyl-2(1H)-quinolinone ethanedioate(1:1); $[\alpha]_D^{20}$=−18.87° (c=1% in methanol) (comp. 24).

b) Compound 14 (4 g) was separated (into its enantiomers) and purified by chiral column chromatography over Chiralcel OD (25 cm; eluent: 100% ethanol; flow: 0.5 ml/min; wavelength: 220 nm). The pure (A)-fractions were collected, and the solvent was evaporated. This residue was dissolved in DCM (100 ml), filtered, and the filtrate was evaporated. The residue was stirred in DIPE (100 ml), filtered off and dried, yielding 1.3 g (A)-6-[amino(4-chlorophenyl)(1-methyl-1H-imidazol-5-yl)methyl]-4-(3-chlorophenyl)-1-methyl-2(1H)-quinolinone (comp. 74). The pure (B)-fractions were collected and evaporated. The residue was crystallized from 2-propanol. The precipitate was filtered off, yielding 1.3 g (B)-6[amino(4-chlorophenyl)(1-methyl-1H-imidazol-5-yl)methyl]-4-(3-chlorophenyl)-1-methyl-2(1H)-quinolinone ($[\alpha]_D^{20}$=+22.86° (c=49.22 mg/5 ml in methanol) (comp. 75).

Example B.9

Air was bubbled through a solution of compound (47) (3.6 g) in THF (40 ml) for 30 minutes. 2-Methyl-2-propanol potassium salt (4.4 g) was added. The mixture was stirred at room temperature for 3 hours, hydrolyzed and then extracted with DCM. The organic layer was separated, dried ($MgSO_4$), filtered and the solvent was evaparated, yielding 2.9 g of product. The product was purified by column chromatography over silica gel (eluent: $CH_2Cl_2/CH_3OH/NH_4OH$ 97.5/2.510.1). The pure fractions were collected and the solvent was evaporated. The residue was crystallized from 2-propanone/DIPE. The precipitate was filtered off and dried, yielding 1.3 g (35%) of (±)-4-(3-chlorophenyl)-6-[(4-chlorophenyl)hydroxy(1-methyl-1H-imidazol-4-yl)methyl]-1-methyl-2(1H)-quinolinone (comp. 48).

Example B.10

A mixture of (±)-4-[(4-chlorophenyl)(1,2-dihydro-1-methyl-2-oxo-4-phenyl-6-quinolinyl)hydroxymethyl]-N,N-dimethyl-1H-imidazole-1-sulfonamide (2.4 g) in hydrochloric acid (10 ml), water (30 ml) and methanol (15 ml) was stirred and heated at 110° C. for 14 hours. The mixture was cooled, basified with $NH_3$ (aq.) and extracted with DCM. The organic layer was dried ($MgSO_4$), filtered off and evaporated till dryness. The residue was purified by column chromatography over silica gel (eluent: $CH_2Cl_2/CH_3OH/NH_4OH$ 95/5/0.2). The pure fractions were collected and evaporated. The residue (1.25 g) was crystallized from 2-propanone/DIPE, yielding 1 g (48.3%) of (±)-6-[(4-chlorophenyl)hydroxy(1H-imidazol-4-yl)methyl]-1-methyl-4-phenyl-2(1H)-quinolinone monohydrate (comp. 43).

Example B.11

Compound (3) (4 g) was dissolved in DCM (10 ml) and acetic acid (5.6 ml) at 45° C. Zinc chloride (5.5 g), followed by cyanoacetic acid (3.5 g) were added. The mixture was stirred at 120° C. for 3 hours and then at 160° C. for 10 hours. Water was added and the mixture was extracted with DCM. The organic layer was washed with $K_2CO_3$ 10%, dried ($MgSO_4$), filtered, and the solvent was evaporated. The residue was purified by column chromatography over silica gel (eluent: $CH_2Cl_2/CH_3OH/NH_4OH$ 96/4/0.2), crystallized from 2-propanone/DIPE, filtered off and dried, yielding 1.95 g (45%) of (±)-4-(3-chlorophenyl)-β-(4-chlorophenyl)-1,2-dihydro-1-methyl-β-(1-methyl-1H-imidazol-5-yl)-2-oxo-6-quinolinepropanenitrile; (comp. 25, mp. 151.3° C.).

Example B.12

Sulfuric acid (1 ml) was added dropwise to acetonitrile (30 ml), while stirring. Compound 3 (3 g) was added. The mixture was stirred at 80° C. for 3 hours and then cooled. $K_2CO_3$ 10% was added and the mixture was extracted with ethyl acetate. The organic layer was separated, dried ($MgSO_4$), filtered and the solvent was evaporated till dryness. The residue (3.58 g) was dissolved in 2-propanone and converted into the ethanedioic acid salt (1:1). The precipitate was filtered off, dried and crystallized from 2-propanone/$CH_3OH$. The precipitate was filtered off and dried, yielding 3.5 g (92%) of (±)-N-[(4-chlorophenyl)[4-(3-chlorophenyl)-1,2-dihydro-1-methyl-2-oxo-6-quinolinyl](1-methyl-1H-imidazol-5-yl)methyl]acetamide ethanedioate (1:1) (comp. 56).

Example B.13

$NH_3$ (aq.) (40 ml) was added at room temperature to a mixture of intermediate 4 (7 g) in THF (40 ml). The mixture was stirred at 80° C. for 1 hour, then hydrolyzed and extracted with DCM. The organic layer was separated, dried ($MgSO_4$), filtered and the solvent was evaporated. The residue was purified by column chromatography over silica gel (eluent: toluene/2-propanol/$NH_4OH$ 80/20/1). The pure fractions were collected and the solvent was evaporated, yielding 4.4 g (±)-6-[amino(4-chlorophenyl)(1-methyl-1H-imidazol-5-yl)methyl]-4-(3-chlorophenyl)-1-methyl-2(1H)-quinolinone (comp. 14).

Example B.14

A solution of compound 36 (6.2 g) in DCM (140 ml) was cooled and tribromoborane (32 ml) was added dropwise. The mixture was stirred at room temperature for tho days. The mixture was poured out into ice water, basified with $NH_3$ (aq.) and extracted with $CH_2Cl_2/CH_3OH$. The organic layer was separated, dried ($MgSO_4$), filtered and the solvent was evaporated till dryness, yielding 6 g (100%) of (±)-6-[(4-chlorophenyl)hydroxy(1-methyl-1H-imidazol-5-yl)methyl]-4-(3-hydroxyphenyl)-1-methyl-2(1H)-quinolinone (comp. 54).

Example B.15

A mixture of compound 54 (2.5 g), 2-chloro-N,N-dimethyl-ethanamine (1.9 g) and potassium carbonate (2.2 g) in ACN (50 ml) and DMF (50 ml) was stirred at 100° C. overnight. The solvent was evaporated till dryness. The residue was taken up in $CH_2Cl_2$/water and decanted. The organic layer was dried, filtered and the solvent was evaporated. The residue (2.7 g) was purified by column chromatography over silica gel (eluent: $CH_2Cl_2/CH_3OH/NH_4OH$ 97/3/0.1 to 90/10/0.1). The pure fractions were collected and the solvent was evaporated. The residue was converted into the ethanedioic acid salt (1:1) in 2-propanone. The precipitate was filtered off, washed with 2-propanone/diethyl ether and dried. The residue was converted into the free base. The precipitate was filtered off and dried. The residue was crystallized from diethyl ether. The precipitate was filtered off and dried, yielding 0.35 g (12%) of (±)-6-[(4-chlorophenyl)hydroxy(1-methyl-1H-imidazol-5-yl)methyl]-4-[3-[2-(dimethylamino)ethoxy]-phenyl]-1-methyl-2(1H)-quinolinone (comp. 62).

Example B.16

$P_4S_{10}$ (12 g) was added to a mixture of compound 90 (6 g) in pyridine (72 ml). The mixture was stirred and refluxed for 6 hours. Ice water was added. The precipitate was filtered off, washed with water and taken up in DCM. The organic layer was separated, dried ($MgSO_4$), filtered and the solvent was evaporated till dryness. The residue was purified by column chromatography over silica gel (eluent: $CH_2Cl_2$/$CH_3OH$/$NH_4OH$ 97.5/2.5/0.1). The pure fractions were collected and the solvent was evaporated. The residue was crystallized from 2-propanone/diethyl ether. The precipitate was filtered off and dried, yielding 1 g of (±)-4-(3-chlorophenyl)-6-[(4-chlorophenyl)(1-methyl-1H-imidazol-5-yl)methyl]-1-methyl-2(1H)-quinolinethione (comp. 128).

Example B.17

A mixture of ethyl malonyl chloride (6.4 ml) in DCM (50 ml) was added dropwise at room temperature to a solution of intermediate (6-d) (15 g) and pyridine (10.7 ml) in DCM (150 ml). The mixture was stirred at room temperature overnight. Water was added and the mixture was decanted. The organic layer was dried ($MgSO_4$), filtered and the solvent was evaporated. The residue (21 g) was purified by column chromatography over silica gel (eluent: $CH_2Cl_2$/2-propanol/$NH_4OH$ 92/8/0.4). The desired fractions were collected and the solvent was evaporated, yielding 10.9 g (60%) of (±)-ethyl 4-(3-chlorophenyl)-6[[(4-chlorophenyl)hydroxy(1-methyl-1H-imidazol-5-yl)methyl]-1,2-dihydro-2-oxo-3-quinolinecarboxylate (comp. 144).

Example B.18 a) A mixture of benzoyl chloride (3.1 ml) in DCM (25 ml) was added dropwise at room temperature to a solution of interm. (6-d) (7 g) and pyridine (5 ml) in DCM (70 ml). The mixture was stirred at room temperature for 45 minutes. Water was added and the mixture was decanted. The organic layer was dried ($MgSO_4$), filtered and the solvent was evaporated, yielding 8.8 g of (±)-N-[2-(3-chlorobenzoyl)-4-[(4-chlorophenyl)hydroxy(1-methyl-1H-imidazol-5-yl)methyl]phenyl]benzeneacetamide (interm. 7). The product was used without further purification.

b) Potassium tert-butoxide (8.7 g) was added to a mixture of intermediate 7 (8.8 g) in DME (70 ml). The mixture was stirred at 50° C. for 3 hours. Water (5 ml) was added and the solvent was evaporated, yielding 8.5 g of (±)-4-(3-chlorophenyl)-6-[(4-chlorophenyl)hydroxy(1-methyl-1H-imidazol-5-yl)methyl]-3-phenyl-2(1H)-quinolinone (comp. 140).

Example B.19

$NH_3$ (aq.) (150 ml) was cooled to 5° C. A solution of (±)-4-(3-chlorophenyl)-1-methyl-6-[1-(4-methylphenyl)-1-(4-methyl-4H-pyrrol-3-yl)ethyl]-2(1H)-quinolinone hydrochloride (16.68 g) in THF (150 ml) was added. The mixture was stirred at room temperature for 2 hours, decanted and extracted with ethyl acetate. The organic layer was dried ($MgSO_4$), filtered and the solvent was evaporated till dryness. The reaction was carried out twice. The residues were combined and purified by column chromatography over silica gel (eluent: toluene/2-propanol/$NH_4OH$ 70-29-1). The pure fractions were collected and the solvent was evaporated. The residue was crystallized from $CH_2Cl_2$/$CH_3OH$/$CH_3CN$. The precipitate was filtered off and the mother layer was evaporated till dryness, purified by column chromatography (eluent: $CH_3OH$/$NH_4OAc$ (0.5% in $H_2O$) 70/30). Two pure fractions were collected and their solvents were evaporated till dryness. Fraction 2 was recrystallized from $CH_2Cl_2$/diethyl ether. The precipitate was filtered off and dried, yielding 0.8 g of (±)-6-[amino(4-chlorophenyl)(1-methyl-1H-imidazol-5-yl)methyl]-3-chloro-4-(3-chlorophenyl)-1-methyl-2(1H)-quinolinone (comp. 143).

Example B.20

Sulfuric acid (1 ml) was added at room temperature to a solution of compound 3 (3.5 g) in methoxyacetonitrile (10 ml) and the mixture was stirred and heated at 80° C. for 3 hours. The mixture was coupled, poured into ice, basified with $NH_3$ (aq.) and filtered off. The precipitate was taken up in DCM. The organic layer was separated, dried, ($MgSO_4$), filtered and the solvent was evaporated. The residue was purified by column chromatography over silica gel (eluent: $CH_2Cl_2$/$CH_3OH$/$NH_4OH$ 96/4/0.3). The pure fractions were collected and the solvent was evaporated. The residue was converted into the hydrochloric acid salt (1:1) and crystallized from ACN. The precipitate was filtered off and dried, yielding 2.5 g (58%) of (±)-N-[(4-chlorophenyl)[4-(3-chlorophenyl)-1,2-dihydro-1-methyl-2-oxo-6-quinolinyl](1-methyl-1H-imidazol-5-yl)methyl]-2-methoxyacetamide monohydrochloride (comp. 89).

Example B.21

A solution of intermediate (4) (3.3 g) in THF (10 ml) was added dropwise at room temperature to a solution of methanamine in water (40 ml). The mixture was stirred at 80° C. for 45 minutes, taken up in water and extracted with DCM. The organic layer was separated, dried ($MgSO_4$), filtered and the solvent was evaporated. The residue was purified by column chromatography over silica gel (eluent: $CH_2Cl_2$/$CH_3OH$/$NH_4OH$ 97/3/0.3 and 95/5/0.3). The pure fractions were collected and the solvent was evaporated. The residue was crystallized from diethyl ether. The precipitate was filtered off and dried, yielding 0.89 g (28%) of (±)-4-(3-chlorophenyl)-6-[(4-chlorophenyl)(methylamino)(1-methyl-1H-imidazol-5-yl)methyl]-1-methyl-2(1H)-quinolinone monohydrate (comp. 61).

Tables 1 to 8 list the compounds that were prepared according to one of the above Examples and table 9 lists both the experimental (column heading "exp.") and theoretical (column heading "theor.") elemental analysis values for carbon, hydrogen and nitrogen of the compounds as prepared in the experimental part hereinabove.

TABLE 1

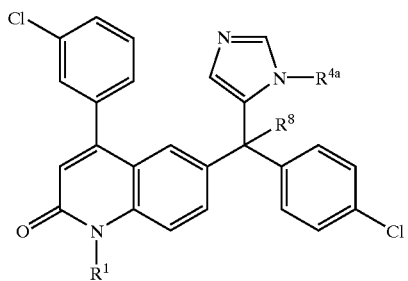

| Co. No. | Ex. No. | R¹ | R⁴ᵃ | R⁸ | Physical data |
|---|---|---|---|---|---|
| 3 | B.1 | CH$_3$ | CH$_3$ | OH | mp. 233.6° C. |
| 4 | B.3 | CH$_3$ | CH$_3$ | OCH$_3$ | mp. 140–160° C.; .C$_2$H$_2$O$_4$.H$_2$O |
| 5 | B.6 | CH$_3$ | CH$_3$ | H | mp. 165° C.; .C$_2$H$_2$O$_4$.H$_2$O |
| 6 | B.5 | CH$_3$ | CH$_2$CH$_3$ | H | mp. 180° C.; .C$_2$H$_2$O$_4$.1/2H$_2$O |
| 7 | B.2 | H | CH$_3$ | H | mp. 260° C. |
| 8 | B.2 | H | (CH$_2$)$_3$CH$_3$ | OH | — |
| 9 | B.4 | CH$_3$ | (CH$_2$)$_3$CH$_3$ | OH | mp. 174° C. |
| 10 | B.3 | H | CH$_3$ | OCH$_2$COOCH$_2$CH$_3$ | mp. 185° C.; .3/2C$_2$H$_2$O$_4$ |
| 11 | B.3 | CH$_3$ | CH$_3$ | O(CH$_2$)$_2$N(CH$_3$)$_2$ | mp. 120° C. |
| 12 | B.7 | CH$_3$ | CH$_3$ | CH$_3$ | mp. 210° C.; .C$_2$H$_2$O$_4$ |
| 13 | B.7 | CH$_3$ | CH$_3$ | CH$_2$CH$_3$ | mp. 196° C.; .C$_2$H$_2$O$_4$ |
| 14 | B.13 | CH$_3$ | CH$_3$ | NH$_2$ | mp. 220° C. |
| 72 | B.13 | CH$_3$ | CH$_3$ | NH$_2$ | .3/2-(E)-C$_4$H$_4$O$_4$ |
| 73 | B.13 | CH$_3$ | CH$_3$ | NH$_2$ | .2HCl |
| 74 | B.8b | CH$_3$ | CH$_3$ | NH$_2$ | (A) |
| 75 | B.8b | CH$_3$ | CH$_3$ | NH$_2$ | (B) |
| 15 | B.3 | CH$_3$ | CH$_3$ | O(CH$_2$)$_3$OH | mp. 135° C. |
| 16 | B.3 | CH$_3$ | CH$_3$ | O(CH$_2$)$_2$CH$_3$ | mp. 180° C.; .C$_2$H$_2$O$_4$.3/2(H$_2$O) |
| 17 | B.3 | CH$_3$ | CH$_3$ | O(CH$_2$)$_2$O—C$_6$H$_5$ | mp. 144° C.; .3/2(C$_2$H$_2$O$_4$) |
| 18 | B.2 | H | CH(CH$_3$)$_2$ | OH | — |
| 19 | B.4 | CH$_3$ | CH(CH$_3$)$_2$ | OH | mp. 254° C. |
| 20 | B.2 | H | (CH$_2$)$_2$OCH$_3$ | OH | mp. 112° C. |
| 21 | B.4 | CH$_3$ | (CH$_2$)$_2$OCH$_3$ | OH | mp. 192° C. |
| 22 | B.3 | CH$_3$ | CH$_3$ | O(CH$_2$)$_2$OH | mp. 198° C. |
| 23 | B.8a | CH$_3$ | CH$_3$ | OH | mp. 150–200° C.; (A); .C$_2$H$_2$O$_4$ |
| 24 | B.8a | CH$_3$ | CH$_3$ | OH | mp. 150–200° C.; (B); .C$_2$H$_2$O$_4$ |
| 25 | B.11 | CH$_3$ | CH$_3$ | CH$_2$—CN | mp. 154° C. |
| 27 | B.2 | H | (CH$_2$)$_3$OCH$_3$ | OH | — |
| 28 | B.4 | CH$_3$ | (CH$_2$)$_3$OCH$_3$ | OH | mp. 196° C.; .H$_2$O |
| 29 | B.3 | CH$_3$ | CH$_3$ | O(CH$_2$)$_3$OCH$_2$CH$_3$ | mp. 105° C.; .3/2(H$_2$O) |
| 31 | B.2 | H | CH$_3$ | OH | >260° C. |
| 32 | B.6 | CH$_3$ | (CH$_2$)$_2$OCH$_3$ | H | mp. 140° C.; .3/2(C$_2$H$_2$O$_4$) |
| 33 | B.6 | CH$_3$ | (CH$_2$)$_3$OCH$_3$ | H | mp. 180° C.; .HCl |
| 56 | B.12 | CH$_3$ | CH$_3$ | —NHCOCH$_3$ | .C$_2$H$_2$O$_4$ |
| 58 | B.11 | CH$_3$ | CH$_3$ | —CH$_2$COOCH$_2$CH$_3$ | .C$_2$H$_2$O$_4$.3/2(H$_2$O) |
| 60 | B.11 | CH$_3$ | CH$_3$ | 1-imidazolyl | — |
| 61 | B.21 | CH$_3$ | CH$_3$ | —NH—CH$_3$ | mp. 164° C. |
| 65 | B.2 | H | (CH$_2$)$_3$SOCH$_3$ | OH | .H$_2$O |
| 66 | B.13 | CH$_3$ | CH$_3$ | —N(CH$_3$)$_2$ | .2C$_2$H$_2$O$_4$.H$_2$O mp. 160° C. |
| 67 | B.13 | CH$_3$ | CH$_3$ | —NH—(CH$_2$)$_2$OCH$_3$ | mp. 216° C. |
| 68 | B.13 | CH$_3$ | CH$_3$ | —NH—(CH$_2$)$_2$—OH | — |
| 69 | B.7 | CH$_3$ | CH$_3$ | —CH$_2$Cl | .2C$_2$H$_2$O$_4$ mp. 220° C. |
| 70 | B.7 | CH$_3$ | CH$_3$ | —CH$_2$Br | — |
| 71 | * | CH$_3$ | CH$_3$ | —CH$_2$OH | .2C$_2$H$_2$O$_4$ |
| 76 | B.4 | —(CH$_2$)$_2$OCH$_3$ | CH$_3$ | OH | mp. 150° C. |
| 77 | * | CH$_3$ | CH$_3$ | —CH$_2$OCH$_3$ | .2C$_2$H$_2$O$_4$ mp. 166° C. |

TABLE 1-continued

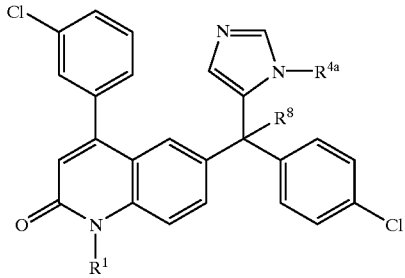

| Co. No. | Ex. No. | $R^1$ | $R^{4a}$ | $R^8$ | Physical data |
|---|---|---|---|---|---|
| 78 | B.13 | $CH_3$ | $CH_3$ | —NH—$OCH_3$ | mp. 170° C. |
| 79 | B.20 | $CH_3$ | $CH_3$ | —NH—$CONH_2$ | .$2H_2O$ |
| 80 | ** | $CH_3$ | $CH_3$ | —$CH_2CONH_2$ | — |
| 81 | B.13 | $CH_3$ | $CH_3$ | —NH—OH | — |
| 82 | B.13 | $CH_3$ | $CH_3$ | —NH$(CH_2)_2N(CH_3)_2$ | — |
| 83 | B.4 | $(CH_2)_2N(CH_3)_2$ | $CH_3$ | OH | .$3/2C_2H_2O_4$ .$3/2H_2O$ mp. 200° C. |
| 84 | * | $CH_3$ | $CH_3$ | —$CH_2N(CH_3)_2$ | .$C_2H_2O_4$ mp. 210° C. |
| 85 | B.4 | $CH_3$ | $CH_3$ | —$N(CH_3)_2$ | — |
| 86 | B.4 | $CH_3$ | $CH_3$ | $NHCOCH_2N(CH_3)_2$ | — |
| 87 | B.4 | $CH_3$ | $CH_3$ | —NH$(CH_2)_9CH_3$ | — |
| 88 | B.4 | $CH_3$ | $CH_3$ | —NH$(CH_2)_2NH_2$ | — |
| 89 | B.20 | $CH_3$ | $CH_3$ | —$NHCOCH_2OCH_3$ | .HCl mp. 220° C. |
| 90 | B.6 | $CH_3$ | $CH_3$ | H | — |
| 91 | B.20 | $CH_3$ | $CH_3$ | —$NHCOCH_2C_6H_5$ | .$C_2H_2O_4.H_2O$ mp. 170° C. |
| 92 | B.20 | $CH_3$ | $CH_3$ | —$NHCOC_6H_5$ | mp. 242° C. |
| 93 | B.20 | $CH_3$ | $CH_3$ | —$NHCOCONH_2$ | .$C_2H_2O_4.H_2O$ mp. 186° C. |
| 94 | B.13 | $CH_3$ | $CH_3$ | —$NHC_6H_5$ | mp. 165° C. |

*: prepared by functional-group transformation of compound 70
**: prepared by functional-group transformation of compound 25

TABLE 2

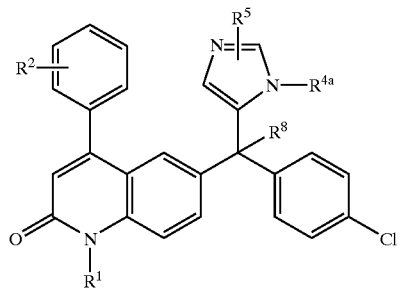

| Co. No. | Ex. No. | $R^1$ | $R^2$ | $R^{4a}$ | $R^5$ | $R^8$ | Physical data |
|---|---|---|---|---|---|---|---|
| 1 | B.1 | $CH_3$ | H | $CH_3$ | H | OH | mp. >250° C. |
| 2 | B.5 | $CH_3$ | H | $CH_3$ | H | H | mp. 100–110° C. |
| 26 | B.1 | $CH_3$ | 3-Cl | $CH_3$ | 2-$CH_3$ | OH | mp. 200° C. |
| 30 | B.6 | $CH_3$ | 3-Cl | $CH_3$ | 2-$CH_3$ | H | mp. 120–140° C.; .$3/2(C_2H_2O_4).H_2O$ |
| 34 | B.1 | $CH_3$ | 3-O—$CH_2$—$CH_3$ | $CH_3$ | H | OH | mp. 190° C. |
| 35 | B.6 | $CH_3$ | 3-O—$CH_2$—$CH_3$ | $CH_3$ | H | H | mp. 160–180° C.; .$HCl.H_2O$ |
| 36 | B.1 | $CH_3$ | 3-O—$CH_3$ | $CH_3$ | H | OH | mp. 210° C. |
| 37 | B.1 | $CH_3$ | 3-O—$(CH_2)_2$—$CH_3$ | $CH_3$ | H | OH | mp. 150–160° C. |
| 38 | B.1 | $CH_3$ | 3-O—$(CH_2)_3$—$CH_3$ | $CH_3$ | H | OH | mp. 150–160° C. |

TABLE 2-continued

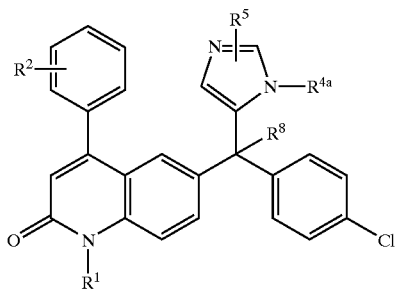

| Co. No. | Ex. No. | $R^1$ | $R^2$ | $R^{4a}$ | $R^5$ | $R^8$ | Physical data |
|---|---|---|---|---|---|---|---|
| 49 | B.1 | $CH_3$ | 4-O—$CH_2$—$CH_3$ | $CH_3$ | H | OH | mp. 184.2° C. |
| 50 | B.1 | $CH_3$ | 3-O—CH—$(CH_3)_2$ | $CH_3$ | H | OH | mp. 147.1° C. |
| 51 | B.6 | $CH_3$ | 3-O—$(CH_2)_3$—$CH_3$ | $CH_3$ | H | H | mp. 164.2° C.; .3/2($C_2H_2O_4$) |
| 52 | B.6 | $CH_3$ | 3-O—$(CH_2)_2$—$CH_3$ | $CH_3$ | H | H | .3/2($C_2H_2O_4$) |
| 53 | B.6 | $CH_3$ | 3-O—CH—$(CH_3)_2$ | $CH_3$ | H | H | mp. 133.9° C.; .$C_2H_2O_4$.$H_2O$ |
| 54 | B.14 | $CH_3$ | 3-OH | $CH_3$ | H | OH | — |
| 64 | B.10 | $CH_3$ | 3-OH | $CH_3$ | H | OH | .HCl.$H_2O$ |
| 55 | B.6 | $CH_3$ | 3-OH | $CH_3$ | H | H | mp. >250° C. |
| 57 | B.1 | $CH_3$ | 2-O$CH_2CH_3$ | $CH_3$ | H | OH | — |
| 59 | B.13 | $CH_3$ | 3-O$CH_2CH_3$ | $CH_3$ | H | $NH_2$ | — |
| 95 | B.8a | $CH_3$ | 3-O$CH_2CH_3$ | $CH_3$ | H | $NH_2$ | (A) |
| 96 | B.8a | $CH_3$ | 3-O$CH_2CH_3$ | $CH_3$ | H | $NH_2$ | (B) |
| 62 | B.15 | $CH_3$ | 3-O$(CH_2)_2N(CH_3)_2$ | $CH_3$ | H | OH | — |
| 63 | B.11 | $CH_3$ | 3-O$(CH_2)_2$—OH | $CH_3$ | H | OH | — |
| 97 | B.1 | $CH_3$ | 3-$CH_2CH_3$ | $CH_3$ | H | OH | — |
| 98 | B.13 | $CH_3$ | 3-$CH_2CH_3$ | $CH_3$ | H | $NH_2$ | mp. 240° C. |
| 99 | B.1 | $CH_3$ | 3-$(CH_2)_2CH_3$ | $CH_3$ | H | OH | — |
| 100 | B.13 | $CH_3$ | 3-$(CH_2)_2CH_3$ | $CH_3$ | H | $NH_2$ | — |
| 101 | * | $CH_3$ | 3-O—$(CH_2)_2OCH_3$ | $CH_3$ | H | OH | .3/2($C_2H_2O_4$) mp. 193° C. |
| 102 | B.1 | $CH_3$ | 3-$CH_3$ | $CH_3$ | H | OH | mp. >250° C. |
| 103 | B.13 | $CH_3$ | 3-$CH_3$ | $CH_3$ | H | $NH_2$ | — |
| 104 | B.1 | $CH_3$ | 3-Br | $CH_3$ | H | OH | — |
| 105 | B.13 | $CH_3$ | 3-Br | $CH_3$ | H | $NH_2$ | — |
| 106 | B.1 | $CH_3$ | 3-O—$CF_3$ | $CH_3$ | H | OH | — |
| 107 | B.13 | $CH_3$ | 3-O—$CF_3$ | $CH_3$ | H | $NH_2$ | mp. 168° C. |
| 108 | B.1 | $CH_3$ | 3-$C_6H_5$ | $CH_3$ | H | OH | — |
| 109 | B.13 | $CH_3$ | 3-$C_6H_5$ | $CH_3$ | H | $NH_2$ | — |
| 110 | B.1 | $CH_3$ | 3-F | $CH_3$ | H | OH | — |
| 111 | B.13 | $CH_3$ | 3-F | $CH_3$ | H | $NH_2$ | mp. >250° C. |
| 112 | B.1 | $CH_3$ | 3-(E)-CH=CH—$CH_3$ | $CH_3$ | H | OH | mp. >250° C. |
| 113 | B.2 | H | 3-Cl | $CH_3$ | 3-Cl | OH | — |
| 114 | B.4 | $CH_3$ | 3-Cl | $CH_3$ | 3-Cl | OH | — |
| 115 | B.1 | $CH_3$ | 3-Cl | H | 3-$CH_3$ | OH | — |
| 116 | B.4 | $CH_3$ | 3-Cl | $CH_3$ | 3-$CH_3$ | OH | — |

TABLE 2-continued

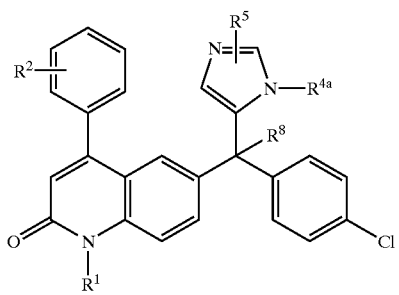

| Co. No. | Ex. No. | R$^1$ | R$^2$ | R$^{4a}$ | R$^5$ | R$^8$ | Physical data |
|---|---|---|---|---|---|---|---|
| 117 | ** | CH$_3$ | 3-CN | CH$_3$ | H | OH | — |
| 160 | B.1 | CH$_3$ | 3-CF$_3$ | CH$_3$ | H | OH | — |

*: prepared by functional-group transformation of compound 54
**: prepared by functional-group transformation of compound 104

TABLE 3

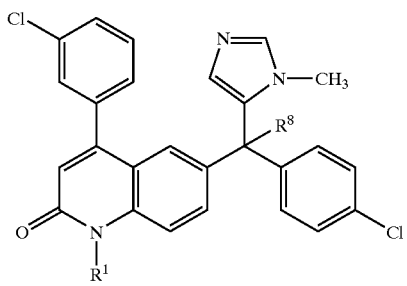

| Co. No. | Ex. No. | R$^1$ | R$^8$ | Physical data |
|---|---|---|---|---|
| 39 | B.4 | CH$_2$CONHCH(COOCH$_3$)(CH$_2$CH(CH$_3$)$_2$) | H | mp. 240° C. (S) |
| 40 | B.4 | CH$_2$-2-quinolinyl | H | mp. 240° C.; .2 HCl |
| 41 | B.4 | CH$_2$CONHCH(COOCH$_3$)(CH$_2$CH(CH$_3$)$_2$) | OH | mp. >260° C. (S) |

TABLE 4

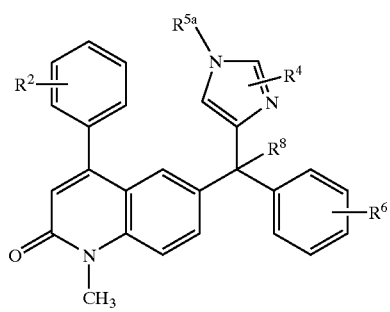

| Co. No. | Ex. No. | R$^2$ | R$^4$ | R$^{5a}$ | R$^6$ | R$^8$ | Physical data |
|---|---|---|---|---|---|---|---|
| 42 | B.6 | H | H | H | 4-Cl | H | mp. 170° C.; .C$_2$H$_2$O$_4$.1/2 H$_2$O |
| 43 | B.10 | H | H | H | 4-Cl | OH | mp. 180° C.; .H$_2$O |
| 44 | B.5 | H | H | CH$_3$ | 4-Cl | H | mp. 152° C. |

TABLE 4-continued

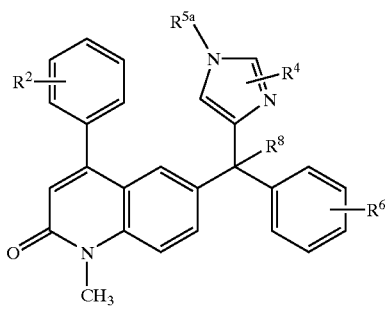

| Co. No. | Ex. No. | R² | R⁴ | R⁵ᵃ | R⁶ | R⁸ | Physical data |
|---|---|---|---|---|---|---|---|
| 45 | B.6 | 3-Cl | H | H | 4-Cl | H | mp. 175° C.; .C₂H₂O₄ |
| 46 | B.5 | 3-Cl | H | CH₂CH₃ | 4-Cl | H | mp. 132° C.; .C₂H₂O₄ |
| 47 | B.5 | 3-Cl | H | CH₃ | 4-Cl | H | mp. 115° C.; .3/2 C₂H₂O₄ |
| 48 | B.9 | 3-Cl | H | CH₃ | 4-Cl | OH | mp. 230° C. |
| 118 | B.4 | 3-Cl | 3-CH₃ | CH₃ | 4-Cl | OH | mp. 222° C. |

TABLE 5

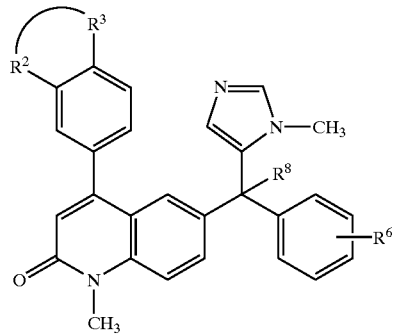

| Co. No. | Ex. No. | —R²—R³— | R⁶ | R⁸ |
|---|---|---|---|---|
| 119 | B.1 | —O—CH₂—O— | 4-Cl | OH |
| 120 | B.13 | —O—CH₂—O— | 4-Cl | NH₂ |
| 121 | B.1 | —O—CH₂—CH₂—O— | 4-Cl | OH |
| 122 | B.13 | —O—CH₂—CH₂—O— | 4-Cl | NH₂ |
| 123 | B.1 | —O—CH=CH— | 4-Cl | OH |

TABLE 6

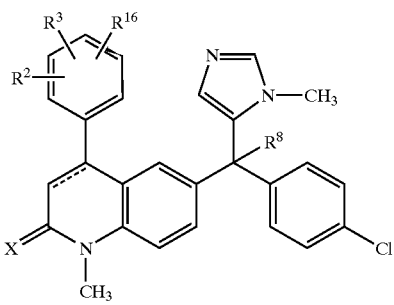

| Co. No. | Ex. No. | X | ═══ | R² | R³ | R¹⁶ | R⁸ | Physical data |
|---|---|---|---|---|---|---|---|---|
| 124 | B.1 | O | double | 3-OCH₃ | 4-OCH₃ | 5-OCH₃ | OH | mp. 230° C. |
| 125 | B.13 | O | double | 3-OCH₃ | 4-OCH₃ | 5-OCH₃ | NH₂ | mp. 218° C. |
| 126 | B.1 | O | single | 3-Cl | H | H | OH | .C₂H₂O₄ mp. 160° C. |
| 127 | B.1 | O | single | 3-Cl | H | H | OH | — |
| 128 | B.16 | S | double | 3-Cl | H | H | H | — |

TABLE 7

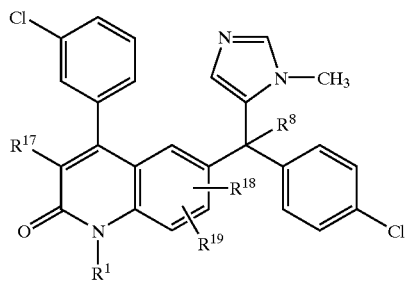

| Co. No. | Ex. No. | R¹ | R¹⁷ | R¹⁸ | R¹⁹ | R⁸ | Physical data |
|---|---|---|---|---|---|---|---|
| 129 | B.17 | H | CN | H | H | H | — |
| 130 | B.4 | CH₃ | CN | H | H | H | mp. 202° C. |
| 131 | B.17 | H | CN | H | H | OH | — |
| 132 | B.4 | CH₃ | CN | H | H | OH | — |
| 133 | B.17 | H | CN | H | H | —CH₂CN | — |
| 134 | B.4 | CH₃ | CN | H | H | —CH₂CN | mp. 138° C. |
| 135 | B.18 | H | CH₃ | H | H | OH | — |
| 136 | B.4 | CH₃ | CH₃ | H | H | OH | — |
| 137 | B.13 | CH₃ | CH₃ | H | H | NH₂ | mp. >250° C. |
| 138 | B.18 | H | C₆H₅ | H | H | H | — |
| 139 | B.4 | CH₃ | C₆H₅ | H | H | H | .3/2(C₂H₂O₄) mp. 180° C. |
| 140 | B.18 | H | C₆H₅ | H | H | OH | — |
| 141 | B.4 | CH₃ | C₆H₅ | H | H | OH | — |
| 142 | B.13 | CH₃ | C₆H₅ | H | H | NH₂ | — |
| 143 | B.13 | CH₃ | Cl | H | H | NH₂ | — |
| 144 | B.17 | H | —COOCH₂CH₃ | H | H | OH | — |
| 145 | B.4 | CH₃ | —COOCH₂CH₃ | H | H | OH | — |
| 146 | B.1 | CH₃ | H | 8-CH₃ | H | OH | — |
| 147 | B.13 | CH₃ | H | 8-CH₃ | H | NH₂ | .H₂O |
| 148 | B.1 | CH₃ | H | 7-Cl | H | OH | — |
| 149 | B.1 | CH₃ | H | 7-CH₃ | H | OH | — |
| 150 | B.1 | CH₃ | H | 5-CH₃ | H | OH | — |
| 151 | B.1 | CH₃ | H | 8-OCH₃ | H | OH | — |
| 161 | B.1 | CH₃ | H | 7-CH₃ | 8-CH₃ | OH | mp. 255° C. |

TABLE 8

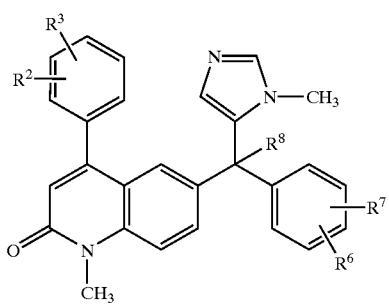

| Co. No. | Ex. No. | R² | R³ | R⁶ | R⁷ | R⁸ | Physical data |
|---|---|---|---|---|---|---|---|
| 152 | B.1 | 3-OCH₂CH₃ | H | 4-OCH₂CH₃ | H | OH | .3/2(C₂H₂O₄) |
| 153 | B.1 | 3-Cl | H | H | H | OH | — |
| 154 | B.1 | 3-Cl | H | 4-CH₃ | H | OH | — |
| 155 | B.1 | 3-Cl | H | 4-OCH₃ | H | OH | — |
| 156 | B.1 | 3-Cl | H | 4-CF₃ | H | OH | — |
| 157 | B.1 | 3-Cl | H | 2-Cl | 4-Cl | OH | — |
| 158 | B.1 | 3-Cl | 5-Cl | 4-Cl | H | OH | — |

TABLE 8-continued

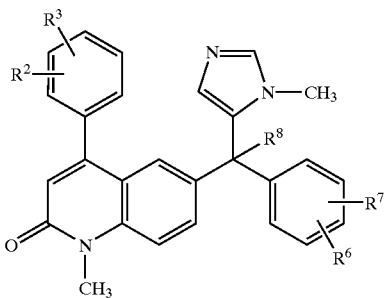

| Co. No. | Ex. No. | R² | R³ | R⁶ | R⁷ | R⁸ | Physical data |
|---|---|---|---|---|---|---|---|
| 159 | B.1 | 3- (4,4-dimethyl-oxazolin-2-yl) | H | 4-Cl | H | OH | — |
| 162 | B.1 | 3-Cl | H | 4-S—CH₃ | H | OH | mp. 169° C. .C₂H₂O₄.H₂O; |
| 163 | B.1 | 3-Cl | H | 4-N(CH₃)₂ | H | OH | mp. decomposes >172° C. |
| 164 | B.1 | 3-Cl | H | —CH=CH—CH=CH—* | | OH | .C₂H₂O₄ |

*: R6 and R7 taken together to form a bivalent radical between positions 3 and 4 on the phenyl moiety

TABLE 9

| Comp. No. | Carbon Exp. | Carbon Theor. | Hydrogen Exp. | Hydrogen Theor. | Nitrogen Exp. | Nitrogen Theor. |
|---|---|---|---|---|---|---|
| 57 | 67.78 | 69.66 | 4.82 | 5.24 | 7.83 | 8.40 |
| 58 | 58.59 | 58.50 | 4.58 | 4.76 | 5.96 | 6.20 |
| 59 | 69.68 | 69.80 | 5.38 | 5.45 | 11.06 | 11.23 |
| 60 | 65.89 | 66.67 | 4.35 | 4.29 | 11.30 | 12.96 |
| 62 | 66.51 | 68.56 | 5.74 | 5.75 | 9.67 | 10.32 |
| 63 | 66.64 | 67.50 | 5.29 | 5.08 | 7.63 | 8.14 |
| 64 | 62.20 | 61.60 | 4.70 | 4.79 | 7.97 | 7.98 |
| 65 | 58.90 | 59.59 | 4.42 | 4.66 | 6.79 | 7.19 |
| 68 | 64.29 | 65.29 | 4.87 | 4.91 | 10.13 | 10.50 |
| 71 | 60.68 | 60.62 | 3.86 | 4.24 | 6.87 | 7.07 |
| 73 | 54.33 | 57.67 | 4.51 | 4.30 | 9.26 | 9.96 |
| 74 | 66.64 | 66.26 | 4.28 | 4.53 | 11.33 | 11.45 |
| 75 | 66.26 | 66.26 | 4.39 | 4.53 | 11.30 | 11.45 |
| 79 | 59.89 | 59.16 | 4.65 | 4.79 | 12.18 | 12.32 |
| 80 | 64.27 | 65.54 | 4.71 | 4.55 | 10.36 | 10.54 |
| 81 | 64.27 | 64.17 | 4.44 | 4.39 | 10.92 | 11.09 |
| 82 | 65.98 | 66.43 | 5.88 | 5.57 | 11.61 | 12.49 |
| 85 | 66.20 | 67.31 | 5.22 | 5.06 | 10.44 | 10.83 |
| 86 | 64.83 | 64.81 | 4.96 | 5.09 | 12.12 | 12.19 |
| 87 | 69.63 | 70.58 | 6.88 | 6.72 | 8.70 | 8.90 |
| 88 | 65.21 | 65.42 | 5.10 | 5.11 | 13.22 | 13.15 |
| 97 | 71.38 | 71.97 | 5.60 | 5.41 | 8.17 | 8.68 |
| 98 | 71.38 | 72.11 | 5.58 | 5.63 | 11.31 | 11.60 |
| 100 | 71.92 | 72.50 | 5.65 | 5.88 | 10.92 | 11.27 |
| 103 | 70.72 | 71.71 | 5.42 | 5.37 | 11.80 | 11.95 |
| 104 | 60.56 | 60.63 | 3.99 | 3.96 | 7.84 | 7.86 |
| 105 | 60.33 | 60.75 | 3.72 | 4.15 | 10.28 | 10.49 |
| 106 | 62.37 | 62.29 | 3.71 | 3.92 | 7.71 | 7.78 |
| 108 | 74.22 | 74.50 | 4.94 | 4.93 | 7.83 | 7.90 |
| 109 | 74.17 | 74.64 | 5.23 | 5.12 | 10.60 | 10.55 |
| 110 | 68.17 | 68.43 | 4.28 | 4.47 | 8.75 | 8.87 |
| 115 | 65.98 | 66.13 | 4.08 | 4.32 | 8.53 | 8.57 |
| 116 | 66.49 | 66.67 | 4.38 | 4.60 | 8.47 | 8.33 |
| 117 | 67.97 | 69.93 | 4.60 | 4.40 | 11.14 | 11.65 |
| 120 | 67.35 | 67.40 | 4.62 | 4.65 | 11.14 | 11.23 |
| 121 | 67.32 | 67.77 | 4.72 | 4.71 | 7.78 | 8.18 |
| 122 | 67.88 | 67.90 | 4.72 | 4.91 | 10.88 | 10.92 |
| 123 | 69.75 | 70.23 | 4.77 | 4.47 | 8.06 | 8.47 |
| 128 | 65.88 | 66.12 | 4.24 | 4.32 | 8.37 | 8.57 |
| 132 | 65.20 | 65.25 | 3.77 | 3.91 | 10.42 | 10.87 |
| 136 | 66.77 | 66.67 | 4.64 | 4.60 | 8.34 | 8.33 |
| 142 | 69.26 | 70.09 | 4.42 | 4.63 | 9.59 | 9.91 |
| 145 | 64.36 | 64.06 | 4.19 | 4.48 | 7.49 | 7.47 |
| 148 | 61.88 | 61.79 | 3.65 | 3.84 | 7.88 | 8.01 |
| 150 | 66.56 | 66.67 | 4.64 | 4.60 | 8.08 | 8.33 |
| 151 | 64.76 | 64.62 | 4.86 | 4.45 | 7.80 | 8.07 |
| 153 | 70.99 | 71.13 | 5.17 | 4.86 | 9.25 | 9.22 |
| 154 | 71.67 | 71.56 | 5.08 | 5.15 | 9.14 | 8.94 |
| 158 | 61.72 | 61.79 | 3.76 | 3.84 | 7.96 | 8.01 |
| 159 | 69.28 | 69.50 | 5.21 | 5.29 | 10.01 | 10.13 |
| 160 | 62.71 | 64.19 | 3.91 | 4.04 | 7.36 | 8.02 |

C. Pharmacological Example

Example C.1

In Vitro Assay for Inhibition of Farnesyl Protein Transferase

Human farnesyl protein transferase was prepared essentially as described (Y. Reiss et al., Methods: A Companion to Methods in Enzymology vol 1, 241–245, 1990). Kirsten virus transformed human osteosarcoma (KHOS) cells (American Type Culture Collection, Rockville, Md., USA) grown as solid tumors in nude mice or grown as monolayer cell cultures were used as a source of human enzyme. Briefly, cells or tumors were homogenized in buffer containing 50 mM Tris, 1 mM EDTA, 1 mM EGTA and 0.2 mM phenylmethylsulfonylfluoride (pH 7.5). The homogenates were centrifuged 28,000×g for 60 min and the supernatants collected. A 30–50% ammonium sulfate fraction was prepared, and the resulting precipitate was resuspended in a small (10 to 20 ml) volume of dialysis buffer containing 20 mM Tris 1 mM dithiothreitol and 20 μM $ZnCl_2$. The ammonium sulfate fraction was dialyzed overnight against two changes of the same buffer. The dialyzed material was applied to a 10×1 cm Q Fast Flow Sepharose (Pharmacia LKB Biotechnology Inc., Piscataway, N.J., USA) which had been preequilibrated with 100 ml of dialysis buffer supplemented with 0.05 M NaCl. The column was washed with an additional 50 ml of dialysis buffer plus 0.05 M NaCl followed by a gradient from 0.05 M to 0.25 M NaCl prepared in dialysis buffer. The enzyme activity was eluted with a linear gradient of 0.25 to 1.0 M NaCl prepared in the dialysis buffer. Fractions containing 4 to 5 ml volumes of column eluate were collected and analyzed for farnesyl protein transferase activity. Fractions with enzyme activity were pooled and supplemented with 100 μM $ZnCl_2$. Enzyme samples were stored frozen at −70° C.

The activity of farnesyl protein transferase was measured using the Farnesyl Transferase [$^3$H] Scintillation Proximity Assay (Amersham International plc., England) under the conditions specified by the manufacturer. To assay for inhibitors of the enzyme, 0.20 μCi of the [$^3$H]-farnesylpyrophosphate substrate and the biotinylated lamin B peptide substrate (biotin-YRASNRSCAIM) were mixed with test compounds in a reaction buffer consisting of 50 mM HEPES, 30 mM $MgCl_2$, 20 mM KCl, 5 mM dithiothreitol, 0.01% Triton X-100. Test compounds were delivered in a 10 μl volume of dimethylsulfoxide (DMSO) to achieve concentrations of 1 and 10 μg/ml in a final volume of 100 μl. The reaction mixture was warmed to 37° C. The enzyme reaction was started by adding 20 μl of diluted human farnesyl protein transferase. Sufficient enzyme preparation was added to produce between 4000 to 15000 cpm of reaction product during the 60 min of reaction incubation at 37° C. Reactions were terminated by the addition of STOP/scintillation proximity bead reagent (Amersham). The reaction product [$^3$H]-farnesyl-(Cys)-biotin lamin B peptide was captured on the streptavidin linked scintillation proximity bead. The amount of [$^3$H]-farnesyl-(Cys)-biotin lamin B peptide synthesized in the presence or absence of test compounds was quantified as cpm by counting on a Wallac Model 1480 Microbeta Liquid Scintillation Counter. The cpm of product was considered to be farnesyl protein transferase activity. The protein farnesyl transferase activity observed in the presence of test compound was normalized to farnesyl transferase activity in the presence of 10% DMSO and expressed as per cent inhibition. In separate studies, some test compounds exhibiting 50% or greater inhibition of farnesyl protein transferase activity were evaluated for concentration-dependent inhibition of enzyme activity. The effects of test compounds in these studies were calculated as $IC_{50}$ (concentration of test compound producing 50% inhibition of enzyme activity) using the LGICV50 computer program written by the Science Information Division of R. W. Johnson Pharmaceutical Research Institute (Spring House, Pa., USA) on a VAX computer.

TABLE 10

| Co. No. | $IC_{50}$ (nM) | Co. No. | $IC_{50}$ (nM) |
| --- | --- | --- | --- |
| 1 | 6.0 | 58 | 2.8 |
| 2 | 8.0 | 59 | 0.14 |
| 3 | 1.7 | 60 | 0.62 |
| 4 | 24 | 61 | 1.1 |
| 5 | 25 | 63 | 1.0 |
| 7 | 1.6 | 64 | 11.6 |

TABLE 10-continued

| Co. No. | $IC_{50}$ (nM) | Co. No. | $IC_{50}$ (nM) |
| --- | --- | --- | --- |
| 12 | 4.2 | 66 | 4.0 |
| 15 | 18.4 | 67 | 5.9 |
| 24 | 2.7 | 69 | 3.4 |
| 25 | 2.2 | 71 | 26 |
| 29 | 57 | 74 | 100 |
| 34 | 1.6 | 75 | 0.86 |
| 35 | 0.39 | 95 | 57 |
| 36 | 2.8 | 96 | 0.11 |
| 37 | 10.1 | 97 | 2.9 |
| 39 | 0.59 | 98 | 6.4 |
| 42 | 910 | 99 | 1.7 |
| 45 | 1000 | 100 | 0.52 |
| 52 | 5.7 | 146 | 68 |

Example C.2

"Ras-Transformed Cell Phenotype Reversion Assay"

Insertion of activated oncogenes such as the mutant ras gene into mouse NIH 3T3 cells converts the cells to a transformed phenotype. The cells become tumorigenic, display anchorage independent growth in semi-solid medium and lose contact inhibition. Loss of contact inhibition produces cell cultures which no longer form uniform monolayers. Rather, the cells pile up into multicellular nodules and grow to very high saturation densities in plastic tissue culture dishes. Agents such as protein farnesyl transferase inhibitors which revert the ras transformed phenotype restore the uniform monolayer growth pattern to cells in culture. This reversion is easily monitored by counting the number of cells in tissue culture plates. Transformed cells will achieve higher cell numbers than cells which have reverted to an untransformed phenotype. Compounds which revert the transformed phenotype should produce antitumor effects in tumors bearing ras gene mutations.

Method:

Compounds are screened in tissue culture in NIH 3T3 cells transformed by the T24 activated human H-ras gene. Cells are seeded at an initial density of 200,000 cells per well (9.6 $cm^2$ surface area) in six-well cluster tissue culture plates. Test compounds are immediately added to 3.0 ml cell growth medium in a 3.0 μl volume of DMSO, with a final concentration of DMSO in the cell growth medium of 0.1%. The test compounds are run at concentrations of 5, 10, 50, 100, and 500 nM along with a DMSO treated vehicle control. (In case a high activity is observed at 5 nM, the test compound is tested at even lower concentrations.) The cells are allowed to proliferate for 72 hours. Then the cells are detached in 1.0 ml trypsin-EDTA cell dissociation medium and counted on a Coulter particle counter.

Measurements:

Cell numbers expressed as cells per well are measured using a Coulter Particle Counter.

All cell counts were corrected for the initial cell input density by subtracting 200,000.

Control cell counts=[cell counts from cells incubated with DMSO vehicle −200,000].

Test compound cell counts=[cell counts from cells incubated with test compound −200,000].

$$\text{Test compound \% inhibition} = \left[1 - \frac{\text{test compound cell counts}}{\text{control cell counts}}\right] \times 100\%.$$

$IC_{50}$ (i.e. the test compound concentration required to inhibit enzyme activity by 50%) is calculated if sufficient data are available, summarized in table 11.

TABLE 11

| Co. No. | $IC_{50}$ (nM) | Co. No. | $IC_{50}$ (nM) |
|---|---|---|---|
| 5 | 32 | 88 | 136 |
| 12 | 66 | 89 | 24 |
| 14 | 3.8 | 91 | 47 |
| 22 | 63 | 92 | 218 |
| 23 | 395 | 93 | 45 |
| 24 | 16 | 94 | 62 |
| 25 | 86 | 96 | 0.78 |
| 29 | 345 | 98 | 15 |
| 34 | 3.0 | 100 | 11 |
| 35 | 3.4 | 101 | 366 |
| 39 | 104 | 102 | 24 |
| 40 | 340 | 104 | 4.5 |
| 56 | 23 | 105 | 3.8 |
| 58 | 96 | 107 | 12 |
| 59 | 0.4 | 109 | 409 |
| 60 | 70 | 111 | 16 |
| 61 | 310 | 112 | 18 |
| 63 | 53 | 119 | 46 |
| 66 | 19 | 120 | 7 |
| 67 | 51 | 122 | 133 |
| 68 | 35 | 123 | 41 |
| 69 | 14 | 125 | 128 |
| 71 | 288 | 126 | 208 |
| 72 | 4.6 | 128 | 177 |
| 73 | 6.1 | 130 | 3.2 |
| 74 | 100 | 130 | 547 |
| 75 | 1.7 | 137 | 655 |
| 76 | 18 | 143 | 82 |
| 78 | 4.6 | 146 | 65 |
| 79 | 657 | 148 | 25 |
| 80 | 500 | 152 | 67 |
| 81 | 83 | 153 | 3.5 |
| 83 | 174 | 154 | 4.5 |
| 84 | 231 | 155 | 69 |
| 86 | 91 | 156 | 25 |
| 87 | 251 | 160 | 40 |

Example C.3

"Farnesyl Protein Transferase Inhibitor Secondary Tumor Model"

The enzyme farnesyl protein transferase catalyzes the covalent attachment of a farnesyl moiety derived from farnesyl pyrophosphate to the oncogene product $p21^{ras}$. This directs $p21^{ras}$ to attach to plasma membranes. Once attached to plasma membranes, mutant or oncogenic forms of $p21^{ras}$ will provide a signal for the transformation and uncontrolled growth of malignant tumor cells. Therefore, inhibitors of protein farnesyl transferase will prevent the membrane attachment of $p21^{ras}$ and inhibit growth of ras-transformed tumors.

Nude mice are inoculated with $1 \times 10^6$ of T24 activated human H-ras gene transformed NIH 3T3 fibroblast cells (T24 cells), subcutaneously in the inguinal region. After three days to allow tumors to become established, treatment with test compounds is begun via the oral route. The test compounds are dissolved in a 20% β-cyclodextrin in 0.1 N HCl solution and administered orally as 0.1 ml of compound solution per 10 g mouse body weight. Routinely used doses are 6.25, 12.5 and 25 mg/kg. Body weights and tumor sizes are monitored during the ensuing 15 days of treatment. At the end of treatment, animals are sacrificed and tumors are weighed.

The "mean vehicle treated tumor weight" is defined as the mean tumor weight from 10 to 15 mice treated with the test compound.

The "mean tumor weight" is defined as the mean tumor weight from 10 to 15 mice not treated with the test compound.

$$\% \text{ Reduction final tumor weight} = \left[1 - \frac{\text{mean tumor weight}}{\text{mean vehicle treated tumor weight}}\right] \times 100\%.$$

TABLE 12

| Co. No. | % reduction final tumor weight at a dose of 25 mg/kg bid, po |
|---|---|
| 14 | 66% |
| 34 | 56% |
| 35 | 39% |
| 56 | 42% |
| 59 | 56% |
| 75 | 86% |

D. Composition Examples

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I), a pharmaceutically acceptable acid or base addition salt or a stereochemically isomeric form thereof.

Example D.1

Oral Solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

Example D.2

Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

Example D.3

Film-coated Tablets

Preparation of Tablet Core

A mixture of 100 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10,000 tablets, each comprising 10 mg of the active ingredient.

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension and the whole is homogenated. The tablet cores are coated with the thus obtained mixture in a coating apparatus.

Example D.4

Injectable Solution 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 4 mg/ml of A.I. The solution was sterilized by filtration and filled in sterile containers.

Example D.5

Suppositories

3 Grams A.I. was dissolved in a solution of 3 grams 2,3-dihydroxybutanedioic acid in 25 ml polyethylene glycol 400. 12 Grams surfactant and 300 grams triglycerides were molten together. The latter mixture was mixed well with the former solution. The thus obtained mixture was poured into moulds at a temperature of 37–38° C. to form 100 suppositories each containing 30 mg/ml of the A.I.

What is claimed is:

1. A compound which is an enantiomer of 6-(amino(4-chlorophenyl)(1-methyl-1H-imidazol-5-yl)methyl)-4-(3-chlorophenyl)-1-methyl-2(1H)-quinolinone having an $[\alpha]_D^{20}$ value of +22.86° (c=49.22 mg/5 ml, methanol) or a pharmaceutically acceptable acid addition salt thereof.

2. A pharmaceutical composition comprising an enantiomer of 6-(amino(4-chlorophenyl)(1-methyl-1H-imidazol-5-yl)methyl)-4-(3-chlorophenyl)-1-methyl-2(1H)-quinolinone having an $[\alpha]_D^{20}$ value of +22.86° (c=49.22 mg/5 ml, methanol) or a pharmaceutically acceptable acid addition salt thereof.

* * * * *